United States Patent
Hirayama et al.

(10) Patent No.: US 10,576,297 B2
(45) Date of Patent: Mar. 3, 2020

(54) MAGNETIC FLUX IRRADIATION DEVICES AND COMPONENTS

(71) Applicants: Dai-Ichi High Frequency Co., Ltd., Tokyo (JP); Nanotherapy Co., Ltd., Tokyo (JP)

(72) Inventors: Kotaro Hirayama, Tokyo (JP); Shuichiro Miyata, Tokyo (JP)

(73) Assignees: DAI-ICHI High Frequency Co., Ltd., Chuo-ku (JP); Nanotherapy Co., Ltd., Chuo-ku (JP)

( * ) Notice: Subject to any disclaimer, the term of this patent is extended or adjusted under 35 U.S.C. 154(b) by 497 days.

(21) Appl. No.: 15/022,466

(22) PCT Filed: Sep. 22, 2014

(86) PCT No.: PCT/JP2014/075770
§ 371 (c)(1),
(2) Date: Mar. 16, 2016

(87) PCT Pub. No.: WO2015/041375
PCT Pub. Date: Mar. 26, 2015

(65) Prior Publication Data
US 2016/0317830 A1 Nov. 3, 2016

(30) Foreign Application Priority Data
Sep. 20, 2013 (JP) ................. 2013-196100

(51) Int. Cl.
*A61N 2/02* (2006.01)
*H01F 27/30* (2006.01)
(Continued)

(52) U.S. Cl.
CPC ............... *A61N 2/02* (2013.01); *A61N 2/004* (2013.01); *H01F 3/10* (2013.01); *H01F 7/202* (2013.01);
(Continued)

(58) Field of Classification Search
CPC .............................................. A61N 2/00–2/12
See application file for complete search history.

(56) References Cited

U.S. PATENT DOCUMENTS 5,030,196 A * 7/1991 Inoue ....................... A61N 2/02
361/143
6,520,903 B1  2/2003 Yamashiro
(Continued)

FOREIGN PATENT DOCUMENTS

CN  1846808  10/2006
DE  10332771  3/2005
(Continued)

OTHER PUBLICATIONS

International Application No. PCT/JP2014/075770, International Search Report and Written Opinion, dated Dec. 19, 2014.

*Primary Examiner* — Thaddeus B Cox
(74) *Attorney, Agent, or Firm* — Kilpatrick Townsend & Stockton LLP

(57) ABSTRACT

Magnetic flux irradiation devices having an adjustable or a replaceable magnetic core are provided. Magnetic cores are also provided. Methods and systems for using such devices are also provided. The devices and magnetic cores are configured to permit easily changing an irradiation pattern of the magnetic flux, depending on a positional relation between the magnetic flux irradiation device and the irradiation object.

13 Claims, 11 Drawing Sheets

(51) Int. Cl.
*H01F 27/26* (2006.01)
*H01F 27/255* (2006.01)
*H01F 3/10* (2006.01)
*A61N 2/00* (2006.01)
*H01F 7/20* (2006.01)

(52) U.S. Cl.
CPC .......... *H01F 27/255* (2013.01); *H01F 27/26* (2013.01); *H01F 27/306* (2013.01)

(56) References Cited

U.S. PATENT DOCUMENTS

| | | |
|---|---|---|
| 7,282,479 B2 | 10/2007 | Ito et al. |
| 7,670,676 B2 | 3/2010 | Horiishi et al. |
| 8,214,053 B2 | 7/2012 | Hirayama et al. |
| 2008/0089472 A1 | 4/2008 | Yoon |
| 2009/0319010 A1 | 12/2009 | Hirayama et al. |
| 2011/0165255 A1 | 7/2011 | Kobayashi et al. |
| 2012/0016174 A1 | 1/2012 | De Taboada et al. |
| 2014/0081069 A1* | 3/2014 | Tai .......................... A61N 2/02 600/10 |
| 2015/0119961 A1 | 4/2015 | Kobayashi et al. |

FOREIGN PATENT DOCUMENTS

| | | |
|---|---|---|
| EP | 1036574 | 9/2000 |
| JP | 4734006 | 4/2001 |
| JP | 3737054 | 11/2005 |
| JP | 3767820 | 2/2006 |
| JP | 3783811 | 3/2006 |
| JP | 4097580 | 3/2008 |
| JP | 4255466 | 2/2009 |
| JP | 4338961 | 7/2009 |
| JP | 4731185 | 4/2011 |
| JP | 4966575 | 4/2012 |
| JP | 5031979 | 7/2012 |
| JP | 5321772 | 7/2013 |
| WO | WO 1998/06342 | 2/1998 |
| WO | WO 2005/089869 | 9/2005 |
| WO | WO 2011/089472 | 7/2011 |

* cited by examiner

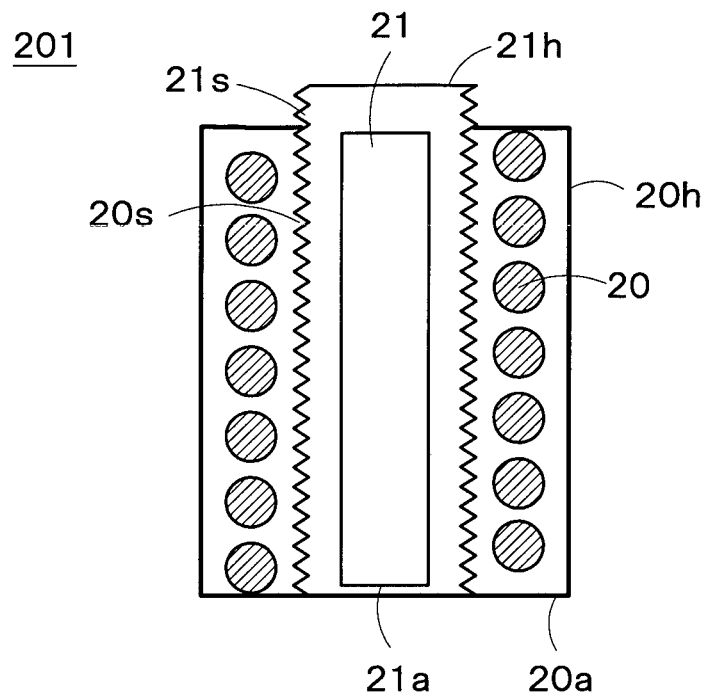
F I G. 1
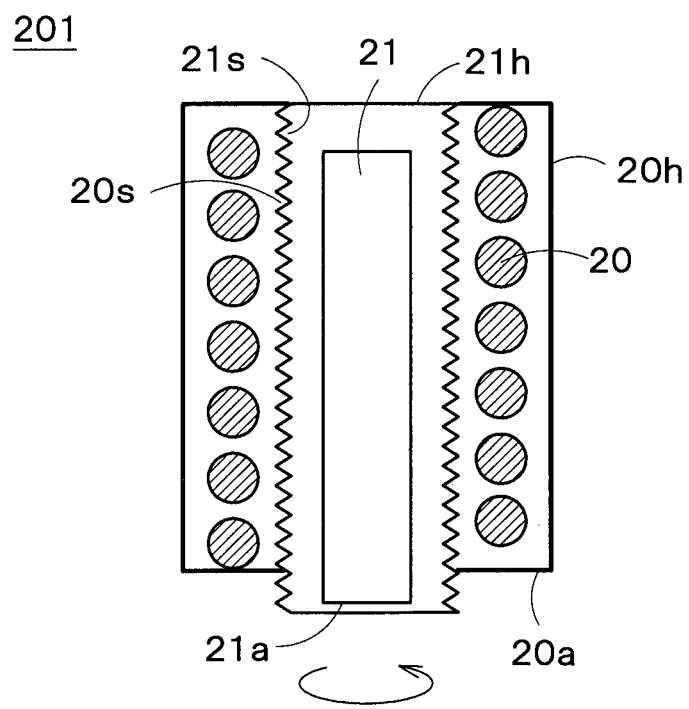
F I G. 2

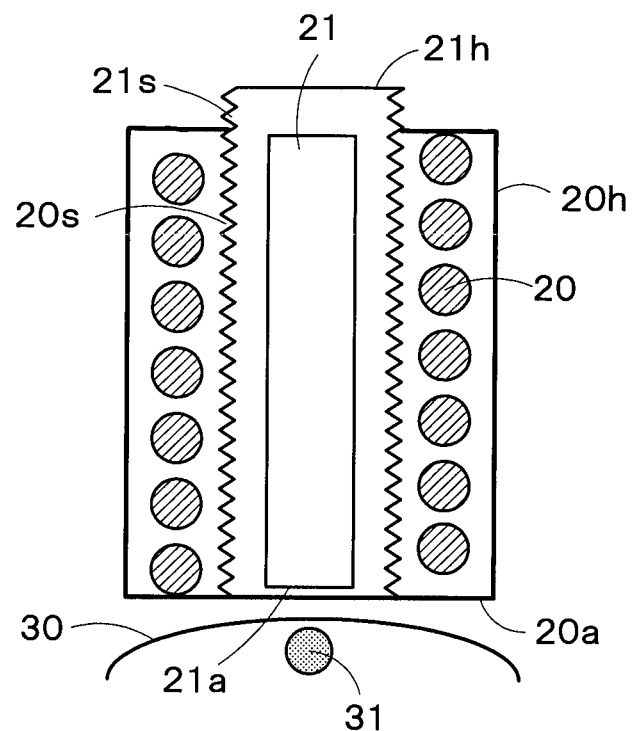
F I G. 3
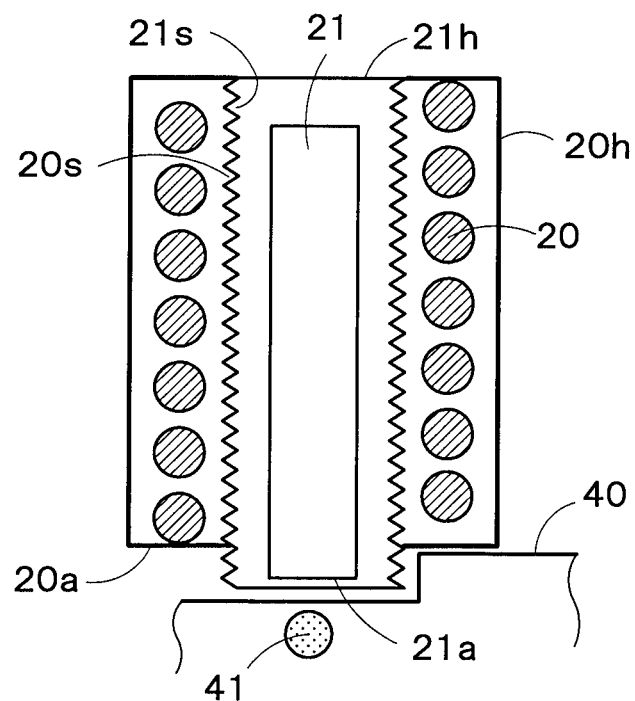
F I G. 4

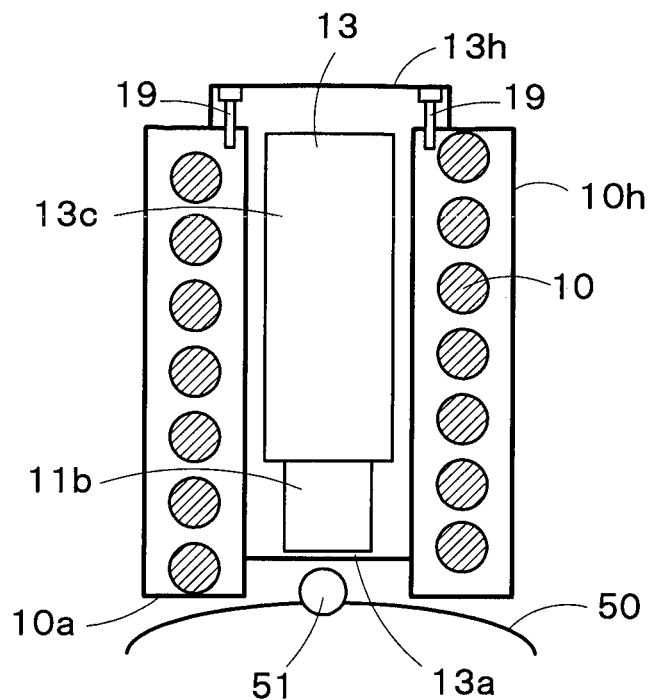
F I G. 11
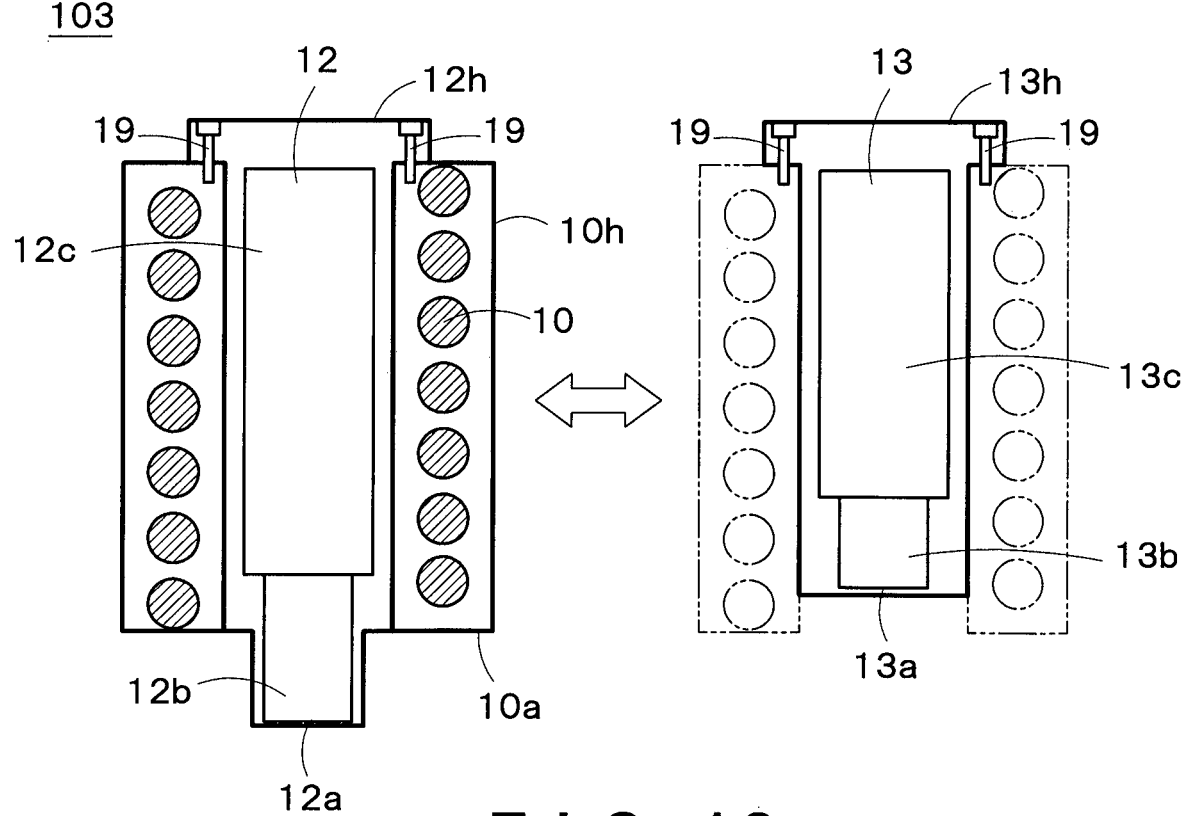
F I G. 12

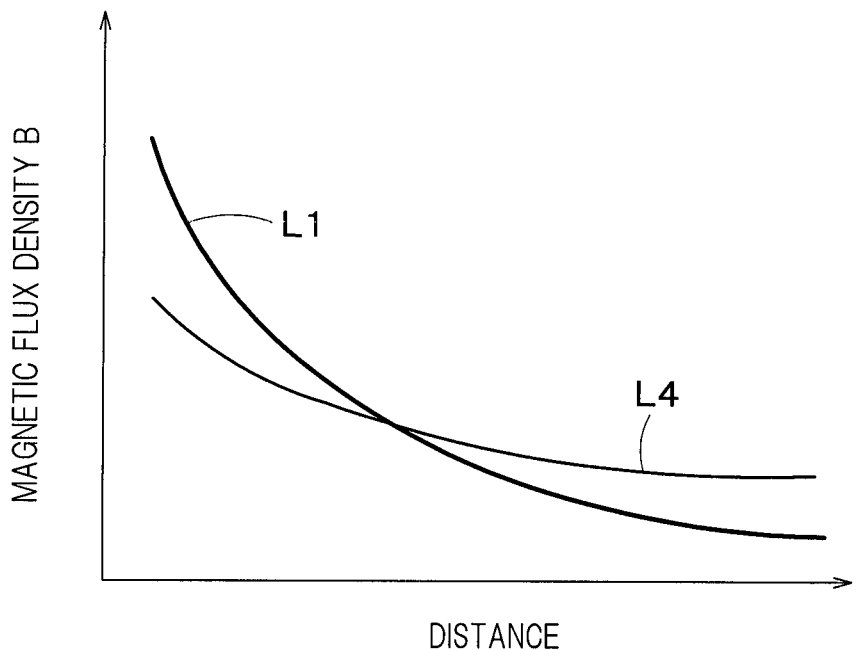
F I G. 15
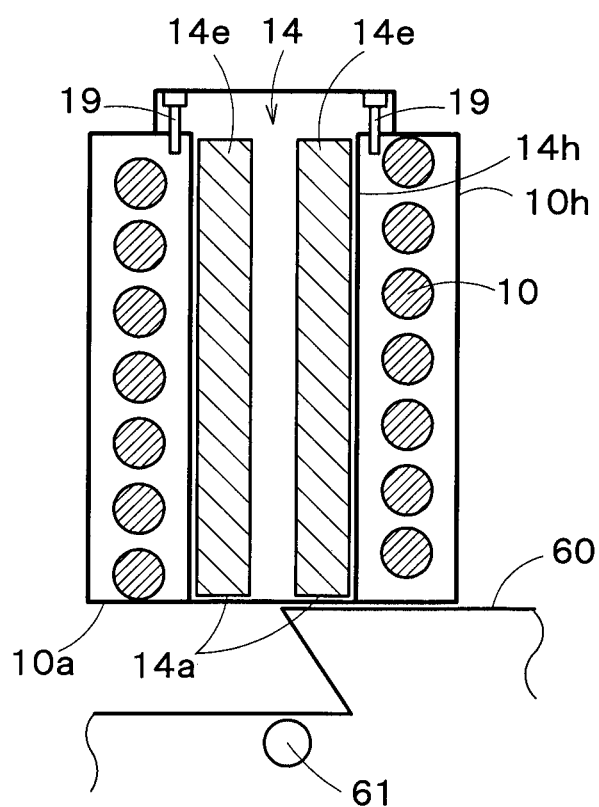
F I G. 16

MAGNETIC FLUX IRRADIATION DEVICES AND COMPONENTS

CROSS-REFERENCE TO RELATED APPLICATIONS

The present application is a § 371 national stage application of International Application No. PCT/JP2014/075770, filed Sep. 22, 2014, which claims the benefit of priority to Japanese Application No. 2013-196100, filed Sep. 20, 2013. Each of these applications are hereby incorporated by reference in their entireties herein.

TECHNICAL FIELD

This disclosure relates to a magnetic flux irradiation device that irradiates magnetic flux from one end of a magnetic core inserted into a coil, by supplying electric current to the coil.

BACKGROUND

Currently, in a local thermotherapy, such as a hyperthermia therapy method, a magnetic flux irradiation device is used to locally heat an affected part. Specifically, the magnetic flux irradiation device has a cylindrical coil, and a magnetic core that is inserted into the coil to be parallel to an axis of the coil When alternating current is supplied to the coil when one end of the magnetic core is disposed to face the affected part, an alternating magnetic flux is irradiated to the affected part from the one end of the magnetic core. Magneto-sensitive heating element particulates that are provided in the affected part generate heat, and the affected part is heated to effect the therapy.

In such a magnetic flux irradiation device, a density of the magnetic flux axially emitted from one end of the magnetic core is significantly attenuated as it goes away from the axis of the coil. Therefore, in order to effectively irradiate the magnetic flux emitted from one end of the magnetic core to the affected part, it is necessary to position the coil sufficiently close to the affected part. However, in conventional magnetic flux irradiation devices, it is not easy to accurately grasp the axis position of the coil from the outside, and it is difficult to accurately position the coil with respect to the affected part.

However, depending on the physical structure of and surrounding the affected part, it may not be possible to bring the one end of the magnetic core sufficiently closer to the affected area. For example, if the affected area is present within an oral cavity, the structure around the affected area may, in some cases, physically interfere with positioning the magnetic core or the coil sufficiently close to the affected area. If the magnetic core or the coil cannot be brought close to the affected area, the magnetic flux emitted from the one end of the magnetic core may be diffused before reaching the affected area, and the magnetic flux density will not be sufficient to effectively irradiate to the affected area.

SUMMARY

The present disclosure provides magnetic flux irradiation devices. In some aspects, the magnetic flux irradiating devices have an adjustable or replaceable magnetic core that irradiate magnetic flux of different magnetic flux densities based on the position or type of the magnetic core.

In one aspect, the disclosure provides magnetic flux irradiating devices having an adjustable magnetic core. In some aspects, the magnetic flux irradiation devices include a cylindrical coil, and a first magnetic core disposed within the cylindrical coil and parallel to an axis of the cylindrical coil, the relative position of the first magnetic core with respect to the cylindrical coil being axially adjustable. In some aspects, the magnetic flux irradiation device is configured to irradiate magnetic flux from the first end of the magnetic core responsive to electric current supplied to the cylindrical coil. In some aspects, the magnetic flux irradiation pattern is based on the relative position of the first end of the magnetic core with respect to a first end of the cylindrical coil.

In another aspect, this disclosure provides a system comprising a magnetic flux irradiation device having an adjustable magnetic core as described above, a power supply configured to supply electrical current to the cylindrical coil of the magnetic flux irradiation device, and a computer configured to control operation of the magnetic flux irradiation device, or process data obtained from monitoring an irradiation target upon which the magnetic flux irradiation device is used, or both.

In another aspect, this disclosure provides methods of irradiating an irradiation target with magnetic flux irradiation, the method comprising providing a magnetic flux irradiation device having an adjustable magnetic core as described above, providing an irradiation target, adjusting the position of the magnetic core with respect to the coil, positioning the irradiation target to face the first end of the magnetic core, and irradiating the irradiation target with magnetic flux by supplying electrical current to the cylindrical coil to generate magnetic flux on the magnetic core that is emitted from the first end of the magnetic core to the irradiation target, wherein the magnetic flux irradiation pattern is based on the relative position of the first end of the magnetic core with respect to a first end of the cylindrical coil.

In one aspect, the disclosure provides magnetic flux irradiating devices having a replaceable magnetic core. In some aspects, the magnetic flux irradiation devices include a cylindrical coil configured to receive a plurality of different magnetic cores. In some aspects, the devices include a first magnetic core disposed within the cylindrical coil and parallel to an axis of the cylindrical coil. In some aspects, the first magnetic core is configured to be detachably connected to the cylindrical coil. In some aspects, the device is configured to irradiate magnetic flux with a first irradiation pattern from the first end of the first magnetic core when electric current is supplied to the cylindrical coil, the first irradiation pattern generated based on the configuration of the first magnetic core.

In another aspect, this disclosure provides a system comprising a magnetic flux irradiation device having a replaceable magnetic core as described above, a power supply configured to supply electrical current to the cylindrical coil of the magnetic flux irradiation device, and a computer configured to control operation of the magnetic flux irradiation device, or process data obtained from monitoring an irradiation target upon which the magnetic flux irradiation device is used, or both.

In another aspect, this disclosure provides methods of irradiating an irradiation target with magnetic flux irradiation, the method comprising providing a magnetic flux irradiation device configured to receive a replaceable magnetic core as described above, selecting a magnetic core to irradiate the irradiation target, inserting the selected magnetic core into a magnetic flux irradiation device, thereby providing a magnetic flux irradiation device having a replaceable magnetic core as described above, positioning the irradiation target to face the first end of the magnetic core, and irradiating the irradiation target with magnetic flux by supplying electrical current to the cylindrical coil to generate magnetic flux on the magnetic core that is emitted from the first end of the magnetic core to the irradiation target, wherein the magnetic flux irradiation pattern of the magnetic core is generated based on the configuration of the magnetic core.

In one aspect, this disclosure provides magnetic flux irradiating devices that are configured to receive an adjustable magnetic core as described above.

In another aspect, this disclosure provides adjustable magnetic cores configured to be positioned within a magnetic flux irradiation device as described above.

In one aspect, this disclosure provides magnetic flux irradiating devices that are configured to receive a replaceable magnetic core as described above.

In another aspect, this disclosure provides replaceable magnetic cores configured to be detachably connected with a magnetic flux irradiation device as described above.

An object achieved by the magnetic flux irradiating device described in this disclosure is to provide a magnetic flux irradiation device that is capable of easily changing an irradiation pattern of the magnetic flux, depending on a positional relation with respect to an irradiation target.

BRIEF DESCRIPTION OF DRAWINGS

FIG. 1 is a schematic side cross-sectional view illustrating a magnetic flux irradiation device according to a first example.

FIG. 2 is a schematic side cross-sectional view illustrating a state in which a relative position of the magnetic core with respect to the coil in an axial direction of the coil is adjusted by a desired amount in the magnetic flux irradiation device of FIG. 1.

FIG. 3 is a diagram for illustrating an aspect in which magnetic flux is irradiated from the magnetic core in the magnetic flux irradiation device of FIG. 1.

FIG. 4 is a diagram for illustrating an aspect in which magnetic flux is irradiated from the magnetic core in the magnetic flux irradiation device of FIG. 2.

FIG. 11 is a diagram for illustrating an aspect in which magnetic flux is irradiated from a third magnetic core in the magnetic flux irradiation device of FIG. 10.

FIG. 12 is a schematic side cross-sectional view illustrating a magnetic flux irradiation device according to a fifth example.

FIG. 15 is a graph for illustrating a density of the magnetic flux irradiated from the first magnetic core and the fourth magnetic core in the magnetic flux irradiation device of FIG. 13.

FIG. 16 is a diagram for illustrating an aspect in which magnetic flux is irradiated from the fourth magnetic core in the magnetic flux irradiation device of FIG. 13.

DETAILED DESCRIPTION

Figure 5:
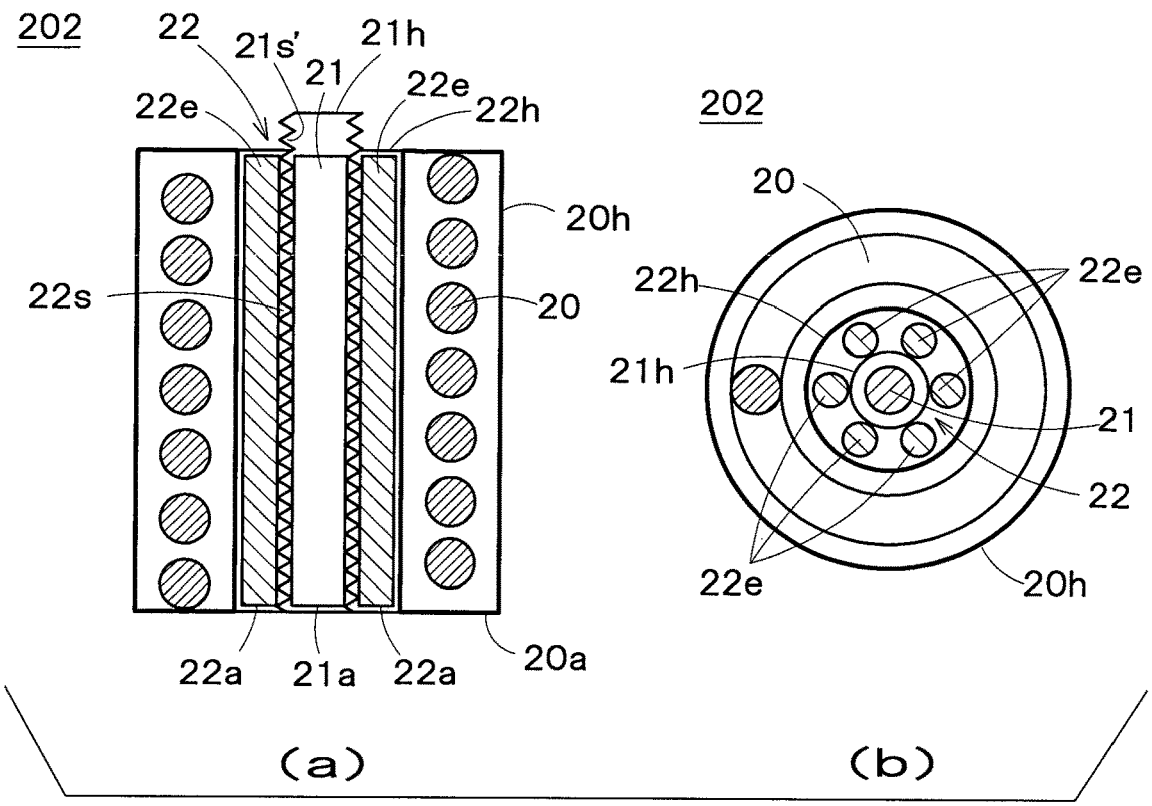
FIG. 5(a) is a schematic side cross-sectional view illustrating a magnetic flux irradiation device according to a second example.
FIG. 5(b) is a top cross-sectional view illustrating the magnetic flux irradiation device of FIG. 5(a).

Certain embodiments and features of the present disclosure relate to magnetic flux irradiating devices having an adjustable or replaceable magnetic core that irradiate magnetic flux of different magnetic flux densities based on the position or type of the magnetic core. Certain embodiments and features relate to systems including such magnetic devices. Certain embodiments and features relate to methods of irradiating an irradiation target using such devices. Certain embodiments and features relate to magnetic flux irradiation devices that are configured to receive an adjustable or replaceable magnetic core that irradiate magnetic flux of different magnetic flux densities based on the position or type of the magnetic core. Certain embodiments and features relate to adjustable magnetic cores or replaceable magnetic cores that, when inserted into a magnetic flux irradiation device, irradiate magnetic flux of different magnetic flux densities based on the position or type of the magnetic core.

In one aspect, a magnetic flux irradiating device includes a cylindrical coil and a magnetic core. The magnetic core may be positioned within the cylindrical coil to be parallel to an axis of the cylindrical coil. In one aspect, the magnetic core may be an adjustable magnetic core, and the position of the magnetic core within the coil can be adjusted axially. The magnetic flux density irradiated from the device may depend on the position of the magnetic core with respect to the coil. In another aspect, the magnetic core may be detachably connected to the device so that the magnetic core can be removed from the device and replaced with a different magnetic core. Magnetic cores having different configurations can be inserted into the coil. The magnetic flux density irradiated from the device may depend on the magnetic core that is inserted into the device. When electric current is supplied to the coil of the device, magnetic flux is generated on the magnetic core and is emitted from one end of the magnetic core.

Two illustrative examples of such devices are provided, followed by a description of common features, which is followed by Sections I and II that provide specific examples for magnetic flux irradiating devices having an adjustable or replaceable magnetic core that irradiate magnetic flux of different magnetic flux densities based on the position or type of the magnetic core.

One illustrative example device includes a cylindrical coil and an adjustable magnetic core that is inserted inside the coil to be parallel to an axis of the coil. When electric current is supplied to the coil, magnetic flux is irradiated from one end of the magnetic core. The magnetic core is disposed within a central cavity defined by the coil. The magnetic core is configured so that the relative position of the magnetic core with respect to the coil in an axial direction of the coil can be adjusted by a desired amount. The diffusion start position of the magnetic flux irradiated from the one end of the magnetic core is adjusted axially with respect to the coil when the relative position of the magnetic core with respect to the coil is axially adjusted. The magnetic flux density of the magnetic flux irradiated from the one end of the magnetic coil may be based on the position of the one end with respect to the coil. Thus, it is possible to easily change the irradiation pattern of the magnetic flux by adjusting the position of the magnetic core within the coil, depending on the relative position of the magnet core with respect to the coil and on the relative position of the magnetic flux irradiation device with respect to the irradiation target.

The coil can be housed within a coil housing having a cavity on an inner peripheral side. Optionally, the magnetic core can be housed within a magnetic core housing inserted inside the cavity.

One way that the magnetic core can be axially adjusted within the coil is if the inner peripheral surface of the coil housing has a screw threading formed thereon, and the outer peripheral surface of the magnetic core (or magnetic core housing) has screw threading formed thereon that matches the screw threading of the coil housing. In this manner, when the coil housing and the magnetic core (or magnetic core housing) are rotated relative to each other about the axis of the coil (for example, by twisting the magnetic core (and magnetic core housing, if present), the relative position of the magnetic core with respect to the coil housed within the coil housing can be easily adjusted by a desired amount in the axial direction of the coil.

There are several other mechanisms that can be used to adjust the axial position of the magnetic core (and magnetic core housing) relative to the coil and coil housing. For example, the axial position may be adjusted using one of the following: a rack and pinion system; a clip system; a molded retention finger system; a wedge system; a ratchet system comprising a teeth component and a pawl component; or a screw system comprising (i) a first screw threaded component attached to the first magnetic core or the first magnetic core housing and (ii) a second screw threaded component attached to the coil, the coil housing, the auxiliary magnetic core, or to the auxiliary magnetic core housing. For example, for the screw system, the first screw threaded component and the second screw threaded component can be matched to each other, and the first screw threaded component and the second screw threaded component may be configured to axially adjust the position of the first magnetic core when the first magnetic core or the magnetic core housing are rotated with respect to the coil, the coil housing, the auxiliary core, or the auxiliary core housing.

The axial position of the adjustable magnetic core may determine the magnetic flux irradiation pattern (such as the magnetic flux density) emitted from the magnetic core within the coil. The axial position of the magnetic core may be adjusted so that a first end of the magnetic core is positioned on the same plane as the first end of the coil. In the context of the adjustable magnetic core, "the same plane" includes a plane located within 1 mm axially inward or outwards from the one end of the coil. The axial position of the magnetic core with respect to the coil may be adjusted so that the one end of the magnetic core protrudes from the one end of the coil. For example, the protrusion may be 50 mm or less. In some instances, the amount of protrusion may be from about 5 mm to about 50 mm or about 10 mm to about 40 mm, or about 15 mm to about 30 mm. In one example the protrusion may be about 20 mm. In another example, up to about half the axial length of the magnetic core may protrude from the one end of the coil. The axial position of the magnetic core with respect to the coil may be adjusted so that the one end of the magnetic core is recessed axially inwards within the coil. For example, the amount of recession may be inwards 1 mm to 10 mm from the one end of the coil.

In addition to the magnetic core, the device having an adjustable magnetic core may also include an auxiliary core that is configured to fit within an internal cavity defined by the coil and the coil housing, the auxiliary magnetic core having a central cavity formed therein that is configured to receive the magnetic core. Optionally, the auxiliary magnetic core may be housed in auxiliary magnetic core housing. The relative position of auxiliary magnetic core and the magnetic core with respect to each other may be axially adjustable. For example, one way that the magnetic core can be axially adjusted with respect to the auxiliary magnetic core is if the inner peripheral surface of the auxiliary magnetic core (or auxiliary magnetic core housing) has a screw threading formed thereon, and the outer peripheral surface of the magnetic core (or magnetic core housing) has screw threading formed thereon that matches the screw threading of the auxiliary magnetic core (or auxiliary magnetic core housing). In this manner, when the auxiliary magnetic core (or auxiliary magnetic core housing) and the magnetic core (or magnetic core housing) are rotated relative to each other about the axis of the coil (for example, by twisting the magnetic core (and magnetic core housing, if present), or twisting the auxiliary magnetic core (or auxiliary magnetic core housing, if present), the relative position of the magnetic core with respect to the auxiliary magnetic core can be easily adjusted by a desired amount in the axial direction of the coil. As discussed in detail above with respect to mechanisms for adjusting the axial position of the magnetic core (and housing) relative to the coil and coil housing, such mechanisms can also be used to adjust the axial position of the magnetic core (and housing) relative to the auxiliary magnetic core (and auxiliary magnetic core housing).

When the device includes a magnetic core housing or an auxiliary magnetic core housing, either housing may be made from a resin containing a magnetic material. For the auxiliary magnetic core housing, at least a portion including the inner peripheral surface may be made of such material. An example magnetic material is resin containing a magnetic material (for example, polyethylene resin mixed with ferrite). According to such an aspect, the magnetic coupling between the auxiliary magnetic core and the magnetic core may be improved, and a focusing effect of the magnetic flux to the magnetic core from the auxiliary magnetic core can be further enhanced.

The auxiliary magnetic core may have a plurality of columnar auxiliary magnetic core elements that are uniformly disposed in a circumferentially within a central cavity defined by the coil. The columnar auxiliary magnetic core elements may be disposed to be to be spaced apart from each other or to abut against each other. The number of columnar auxiliary magnetic core elements may be two, three, four, five, six, seven or more. For example, the number of columnar auxiliary magnetic core elements may be four or six. When the number of magnetic core elements increases and the magnetic core cross-sectional area increases, the magnetic flux density emitted from the magnetic core may be distributed (decline).

A second illustrative example device includes a cylindrical coil and a replaceable magnetic core that is inserted inside the coil to be parallel to an axis of the coil. When electric current is supplied to the coil, magnetic flux is irradiated from one end of the magnetic core. The device is configured to receive magnetic cores of various different configurations. The magnetic core is disposed within a central cavity defined by the coil. The magnetic core is configured so that it can be detachably connected to the coil. A magnetic core is selected based on the characteristics of the irradiation target to be irradiated and on the desired magnetic flux density (irradiation pattern). Based on certain characteristics of the irradiation target to be irradiated or on the desired magnetic flux density, one magnetic core may be selected and inserted into the coil. However, if an irradiation target different characteristics or if the desired magnetic flux density is different, a second magnetic core or third magnetic core may be selected and inserted into the coil. The magnetic core is configured to have specific relative position of the magnetic core with respect to the coil in an axial direction of the coil. The diffusion start position of the magnetic flux irradiated from the one end of the magnetic core depends on the relative position of the magnetic core with respect to the coil when the magnetic core is inserted in the coil. The magnetic flux density of the magnetic flux irradiated from the one end of the magnetic coil may be based on the position of the one end with respect to the coil. Thus, it is possible to easily change the irradiation pattern of the magnetic flux irradiated by the device by replacing the magnetic core that is inserted within the coil, depending on the relative position of the magnet core with respect to the coil and on the relative position of the magnetic flux irradiation device with respect to the irradiation target.

The replaceable magnetic core may be detachably connected to the coil through a variety of mechanisms. When the replaceable magnetic core is detachably connected to the coil, the relative position of the magnetic core is fixed with respect to the position of the coil. The magnetic core may be connected to a coil housing containing the coil, or a core housing containing the magnetic core may be connected to the coil a coil housing containing the coil, or the magnetic core may be connected to another part of the device that has a fixed position with respect to the coil. One way that the magnetic core may be detachably connected to the coil is using a screw made of a nonconductive material (such as resin).

There are several other mechanisms that can be used to detachably connect (attach) the replaceable magnetic cores to the coil. For example, the magnetic cores may be detachably connected to the coil using one of the following mechanisms: a screw made of nonconductive material, a clip system, a molded retention finger system, a wedge system, or a layer of adhesive or sealant. Another mechanism is a screw system that is configured to permit the magnetic core to be screwed into the device. For example, one screw system may include a first screw threaded part attached to the first magnetic core, a second screw threaded part attached to the second magnetic core, and a third screw threaded part attached the cylindrical coil directly or indirectly, wherein the first screw threaded part and the second screw threaded part are matched to the third screw threaded part, and wherein each of the first, second, and third threaded parts are made of nonconductive material. The parts or components of these different various mechanisms may be attached directly to the replaceable magnetic core or the magnetic core housing, the coil housing, or another part of the magnetic flux irradiation device configured to stay in a fixed position. In some instances, the threaded parts may be formed on the magnetic cores, the magnetic core housings, or the coil housing. Each of these mechanisms may allow to be the replaceable magnetic core to be detachably connected to the coil. In some instances, the magnetic cores are inserted and removed from within the coil from a first end of the coil. In other instances, the magnetic core may be removed from the coil through the second (opposite) end of the coil.

When the replaceable magnetic core is detachably connected to the coil, the relative position of the magnetic core with respect to the coil can be kept at a predetermined position. Thus, the magnetic flux irradiated from one end of the magnetic core will have a specific irradiation pattern. When the magnetic core in the device is replaced with a magnetic core having a different configuration, such as one in which the magnetic core is in a different relative position with respect to the coil when the magnetic core is inserted into the device, the magnetic flux irradiated from one end of the magnetic core will have a different specific irradiation pattern.

The device may be configured to receive a replaceable magnetic core in one of many different configurations. Different magnetic core configurations may provide different irradiation patterns. For example, different magnetic core configurations may be configured to emit magnetic flux at different magnetic flux densities. In some examples, different magnetic core configurations may be configured to emit magnetic flux that has different extents of diffusion (attenuation). For instance, the replaceable magnetic core may have a uniform cross-section. In another instance, the replaceable magnetic core may have a columnar portion of a small cross-sectional area that defines the one end portion, and a columnar portion of a large cross-sectional area adjacent to the columnar portion of the small cross-sectional area. The large cross-sectional columnar portion and the small cross-sectional columnar portion of the magnetic core may be a single magnetic core component or may be two adjoined magnetic core components. Where the magnetic core has this configuration, the magnetic flux irradiated from the one end portion of the magnetic core is focused by the columnar portion of the small cross-sectional area of the magnetic core, and the magnetic flux density may be enhanced. Also, where the magnetic core has this configuration and is inserted within the device, the one end portion of the magnetic core may be positioned on the same plane as the one end portion of the coil, or may protrude axially outward from the one end portion of the coil, or may recede axially inward from the one end portion of the coil. In another instance, the replaceable magnetic core may have a plurality of columnar magnetic core elements that can be disposed circumferentially within a central cavity defined by the coil.

Where the magnetic core has this configuration, the magnetic flux emitted axially from the one end of the magnetic core is less likely to be diffused (magnetic flux density is less likely to be attenuated).

In various magnetic core configurations, the one end of the magnetic core may be positioned on the same plane as the first end of the coil. In the context of the replaceable magnetic core, "the same plane" includes a plane located within 1 mm axially inward or outwards from the one end of the coil. In another configuration, the one end of the magnetic core may protrude from the one end of the coil. For example, the protrusion may be 50 mm or less. In some instances, the amount of protrusion may be from about 5 mm to about 50 mm or about 10 mm to about 40 mm, or about 15 mm to about 30 mm. In one example the protrusion may be about 20 mm. In another example, up to about half the axial length of the magnetic core may protrude from the one end of the coil. In another configuration, the one end of the magnetic core is recessed axially inwards within the coil. For example, the amount of recession may be inwards 1 mm to 10 mm from the one end of the coil.

The magnetic flux density irradiated from the one end of the magnetic core may be determined based on the position of the one end of the magnetic core in relation to the one end of the coil. In one instance, where the one end portion of the magnetic core protrudes axially outward from the one end portion of the coil, the diffusion start position of the magnetic flux irradiated from the one end portion of the magnetic core is extended, and it may be possible to more effectively irradiate the magnetic flux (for example, with respect to an irradiation target portion to which a magnetic core having a different configuration cannot be brought sufficiently close). In another instance, where the one end portion of the magnetic core recedes axially inwards from the one end portion of the coil, a recess may be formed within the coil between the first end of the coil and the one end of the magnetic core in which a strong magnetic flux can be formed by the coil, and it may be possible to more effectively irradiate the magnetic flux (for example, with respect to an irradiation target that can be inserted inside the recess). In another instance, where the magnetic core has a plurality of magnetic core elements, the diffusion of the magnetic flux irradiated from the one end portion of the magnetic core can be suppressed (reduced), and it may be possible to effectively irradiate the magnetic flux to a distant irradiation target (for example, with respect to an irradiation target portion to which a magnetic core having a different configuration cannot be brought sufficiently close).

Different irradiation patterns may be emitted from the magnetic flux irradiation device base do the configuration of the replaceable magnetic core inserted within the coil. An irradiation pattern may include at least a magnetic flux density or an extent of diffusion (attenuation). For example, depending on the configuration of the magnetic core, the magnetic flux density emitted from the magnetic core may be about 0.5 mT to about 30 mT, or about 5 mT to about 20 mT, or about 10 mT to about 30 mT, or about 8 mT to about 25 mT. For example, the magnetic flux density may be about 10 mT, about 12 mT, about 15 mT, about 18 mT, about 20 mT, about 23 mT, about 25 mT, about 28 mT, or about 30 mT. In some instances, the magnetic flux density that irradiates the irradiation target depends on the axial position of the one end of the magnetic core relative to the one end of the coil. The magnetic flux density emitted from the magnetic core may be based on the size of the coil and the magnetic core, the configuration of the magnetic core, and/or the frequency supplied to the coil.

For the two illustrative example devices described above, the size of the coil may be selected based on various factors, including the desired magnetic flux density, the frequency (power) to be provided to the coil, and the maximum temperature that can be dissipated. For example, based on the desired characteristics of the coil and the device, the diameter of the coil may be about 35 mm to about 140 mm. In another aspect, based on the desired characteristics of the coil and the device, the length of the coil 20 can be about 60 mm to about 240 mm. In one example, the diameter of the coil can be about 70 mm, and the axial length of the coil can be about 120 mm. In another example, the diameter of the coil can be about 35 mm, and the axial length of the coil can be about 60 mm. In another example, the diameter of the coil can be about 140 mm, and the axial length of the coil can be about 240 mm. In some examples, the length of the coil is about 1.5 to about 2.0 times greater than the diameter of the coil. For example, the length of the coil may be about 1.65, about 1.71, about 1.88, or some other fold between about 1.5 to about 2.0, greater than the diameter of the coil. In one example, the length of the coil 10 is about 1.71 greater than the diameter of the coil 10.

The dimensions (size) of the magnetic cores may be selected based on the desired frequency and use for the device. For example, the length of the core may be the same length as, or may have a shorter length than, or may have a longer length than, the coil or the coil housing. In some instances, the length of the magnetic core is about the same as the length of the coil. In one aspect, the diameter of the core may be selected to fit within the diameter of a central cavity defined within the coil and, in particular, a central cavity defined within the coil housing that houses the coil.

For example, where the device has a coil having a diameter of 70 mm and a length of 120 mm, the diameter of the magnetic core may be about 35 mm to about 140 mm. In another example, the axial length of the magnetic core may be about 60 mm to about 240 mm. For example, the magnetic core may have a diameter of about 35 mm and an axial length of about 60 mm. In another example, the magnetic core may have a diameter of about 70 mm and an axial length of about 120 mm. In another example, the magnetic core may have a diameter of about 140 mm and an axial length of about 240 mm. In some instances, the ratio of the length of the magnetic core to the diameter of the magnetic core is about 1:2 to 1:5. For example, the length of the magnetic core may be about 2 times, 3 times, 4 times, or 5 times larger than the diameter of the magnetic core. In one instance, the length of the magnetic core may be about 4 times larger than the diameter of the magnetic core.

In another example, where the device has a coil having a diameter of 70 mm and a length of 120 mm, the columnar portion 11b of the small cross-sectional area may have a diameter of 20 mm and an axial length of 20 mm, and the columnar portion of the large cross-sectional area may have a diameter of 50 mm and an axial length of 100 mm. In some cases, the columnar portion of the small cross-sectional area may be a cylindrical shape having a diameter of 20 mm and an axial length of 20 mm, and the columnar portion of the large cross-sectional area has a cylindrical shape having a diameter of 50 mm and an axial length of 100 mm. In one aspect, the ratio of the diameter of the columnar portion of the small cross-sectional area to the diameter of the columnar portion of the large cross-sectional area may be about 1:2 to 1:3. For example, the diameter of the columnar portion of the small cross-sectional area may be about may be about 2.5 smaller than the columnar portion of the large cross-sectional area.

Where the magnetic core has a plurality of columnar magnetic core elements, the dimensions of the columnar magnetic core elements may be selected to fit within the diameter of a central cavity defined within the coil and, in particular, within a central cavity defined within the coil housing. For example, where a coil is 120 mm in length and a magnetic core includes six columnar magnetic core elements, the diameter of each may be 15 mm and the axial length of each may be 120 mm. In another example, where a coil is 120 mm in length and a magnetic core includes four columnar magnetic core elements, the diameter of each may be 10 mm and the axial length of each may be 120 mm.

An auxiliary magnetic core may be a solid magnetic unit or may include a plurality of auxiliary columnar magnetic core elements. The length of the auxiliary core may generally be about the same as the length of the coil. The diameter of the auxiliary magnetic core may depend on the diameter of the coil, and the diameter of the inner peripheral cavity of the coil housing, and the diameter of the magnetic core (and, if included, the diameter of the magnetic core housing). In general, the dimensions of the auxiliary columnar magnetic core elements may be selected to fit within the diameter of a central cavity defined within the coil and, in particular, within a central cavity defined within the coil housing, and still have sufficient room to accommodate the magnetic core.

The magnetic core and the auxiliary magnetic core may be formed as various shapes. For example, the magnetic core or the auxiliary magnetic core may have a cylindrical shape or a prismatic shape (such as a quadrangular prism). Where the magnetic core has a large cross-sectional columnar portion adjacent to a small cross-sectional columnar portion, the columnar portions may be cylindrical or prismatic.

The magnetic core or the auxiliary magnetic core may be made of a magnetic material that restricts and channels magnetic eddy current fields. For example, the material of the magnetic core can include a Mn—Zn ferrite material, a Ni—Zn material, an iron powder, a high flux powder, a permalloy powder, or an amorphous alloy. In one example, the material of the magnetic core is a Mn—Zn ferrite material. Other magnetic materials are also contemplated for use in making the magnetic cores.

The material of the magnetic core or the auxiliary magnetic core may be selected based on the desired frequency range for the device. For example, a Mn—Zn ferrite material may be selected for a desired frequency of 10 kHz to 2 MHz. In another example, a Ni—Zn material may be selected for a desired frequency range of 200 kHz to 100 MHz. In another example, an iron powder may be selected for a desired frequency range of 100 kHz to 100 MHz. In another example, a high flux powder or a permalloy powder may be selected for a desired frequency range of 10 kHz to 1 Mhz. In another example, an amorphous alloy may be selected for a desired frequency range of 500 Hz to 250 kHz.

The magnetic flux density emitted from the magnetic core of the device may be based on one or more of the size of the coil, the size of the magnetic core, the configuration of the magnetic core, and the frequency of the power supplied to the coil. For example, the magnetic flux density emitted may be about 0.5 mT to about 30 mT. For example, where the size of the coil 10 and the magnetic core 11 are small, the magnetic flux density may range from about 0.5 mT to about 15 mT. In another example, where the size of the coil 10 and the magnetic core 11 are larger, the magnetic flux density may range from about 10 mT to about 30 mT. In certain instances, the magnetic flux density may be based on the size of the coil and the magnetic core, the configuration of the magnetic core, and/or the frequency supplied to the coil.

In use, an irradiation target is positioned to face the first end of the magnetic core in the device. The irradiation target may be position about 5 mm from the first end of the magnetic core. Where the magnetic flux density emitted from the magnetic core is greater (for example, 30 mT), the irradiation target may be positioned up to 15 cm from the first end of the magnetic core. For example, the irradiation target may be positioned at a distance of about 5 mm, 10 mm, 20 mm, 30 mm, 50 mm, 100 mm, or some other distance up to about 15 cm. Where the irradiation target is inserted within the magnetic core, it may be positioned to not be in contact with the magnetic core or any other part of the device.

Electric current (for example, alternating electric current) may be supplied to the coil from a power source at a predetermined frequency (such as about 50 kHz to about 400 kHz). Alternating magnetic flux parallel to the axial direction is formed on the magnetic core (or each of the magnetic core elements) within the coil when alternating current is supplied and is emitted from the one end of the magnetic core. The magnetic flux emitted from the magnetic core can irradiate an irradiation target disposed (positioned) to face the one end of the magnetic core.

The illustrative examples described above have been provided to introduce the subject matter of this disclosure and are not intended to limit the scope of the disclosure. Hereinafter, some examples will be described in detail below with reference to the accompanying drawings but other examples are within the scope of this disclosure. Additional embodiments and features are also described throughout this disclosure. The same reference indicators will be used throughout the drawings and the following description to refer to the same or like items.

I. Magnetic Flux Irradiation Device Having an Adjustable Magnetic Core

FIG. 1 is a schematic side cross-sectional view illustrating a magnetic flux irradiation device according to a first example. FIG. 2 is a schematic side cross-sectional view illustrating a state in which a relative position of the magnetic core with respect to the coil in the axial direction of the coil is adjusted by a desired amount in the magnetic flux irradiation device of FIG. 1.

As illustrated in FIG. 1, a magnetic flux irradiation device 201 according to this example is provided with a cylindrical coil 20, and a magnetic core 21 that is inserted inside the coil 20 to be parallel to an axis of the coil 20.

As illustrated in FIG. 1, the coil 20 may have a cylindrical solenoid coil. For example, a diameter of the coil 20 may be 70 mm, and an axial length of the coil 20 may be 120 mm. As discussed above, coil 20 may have other sizes.

In certain instances, as illustrated in FIG. 1, the magnetic core 21 may have a quadrangular prism shape. For example, a length of one side of the cross-section perpendicular to the axial direction of the magnetic core 21 may be 20 mm, and an axial length may be 120 mm. A material of the magnetic core 21 is, for example, a Mn—Zn ferrite material. As discussed above, magnetic core 21 may have other sizes and or be made of other materials.

A power source (not illustrated) may be electrically connected to the coil 20. When an alternating current is supplied to the coil 20 from the power source at a predetermined frequency (for example, 50 kHz to 400 kHz), the alternating magnetic flux parallel to the axial direction may be formed on the magnetic core 21 inserted inside the coil 20, and the alternating magnetic flux is adapted to be emitted in the axial direction from one end 21a of the magnetic core 21.

In one example, as illustrated in FIGS. 1 and 2, when the magnetic core 21 is inserted inside the coil 20, a relative position of the magnetic core 21 with respect to the coil 20 in the axial direction of the coil 20 can be adjusted by a desired amount.

In one instance, as illustrated in FIGS. 1 and 2, the coil 20 may be housed within a coil housing 20h having a cavity on an inner peripheral side, and the magnetic core 21 may be housed within a magnetic core housing 21h inserted inside the cavity of the coil housing 20h. A coil side screw threading 20s may be formed on an inner peripheral surface of the coil housing 20h, and a magnetic core side screw threading 21s corresponding to the coil side screw threading 20s may be formed on an outer peripheral surface of the magnetic core housing 21h. When the coil housing 20h and the magnetic core housing 21h are relatively rotated about the axis of the coil 20, by the action of the screw threading, the relative position of the magnetic core 21 housed within the magnetic core housing 21h with respect to the coil 20 housed within the coil housing 20h may be easily adjusted by a desired amount in the axial direction of the coil 20. 5

In one example, where the magnetic core 21 has the configuration and dimensions identified above, the adjustable amount of protrusion of the one end 21a of the magnetic core 21 with respect to the one end 20a of the coil 20 may be 50 mm or less. In some instances, when the amount of protrusion is 50 mm or higher, the magnetic flux formed inside the magnetic core 21 may easily escape to the outside from the side surface of the protruding, and the density of the magnetic flux emitted from the one end 21a may be decreased.

Next, the operation of the above-described example will be described.

As illustrated in FIG. 3, in some instances, the relative position of the magnetic core 21 with respect to the coil 20 may be adjusted so that the one end 21a of the magnetic core 21 is located on the same plane as the one end 20a of the coil 20. For example, this adjustment may be appropriate when the one end 21a of the magnetic core 21 may be positioned sufficiently close to the irradiation target 31 (for example, up to the position of 5 mm from the irradiation target 31). In some cases, this configuration may be used to irradiate an irradiation target 31 located inside an irradiation object 30 having a convex surface.

Alternating current may be supplied to the coil 20 from a power source (not illustrated) at a predetermined frequency (for example, 100 kHz). In one aspect, alternating magnetic flux parallel to the axial direction may be formed on the magnetic core 21 positioned inside the coil 20, and the alternating magnetic flux may be emitted toward the irradiation target 31 from the one end 21a of the magnetic core 21. When the one end 21a of the magnetic core 21 may be positioned to be sufficiently close to the irradiation target 31, the irradiation target 31 is effectively irradiated with the magnetic flux, for example, at a magnetic flux density of 20 mT. In one aspect, magneto-sensitive heating particles may be provided to the irradiation target 31 prior to irradiation. In this aspect, the magneto-sensitive heating particles in the irradiation target 31 may be magnetically heated by the magnetic flux, and the irradiation target 31 heated by the heat generation of the magneto-sensitive heating element when exposed to the magnetic flux.

In one instance, as illustrated in FIG. 4, the relative position of the magnetic core 21 with respect to the coil 20 may be adjusted so that one end 21a of the magnetic core 21 projects axially outward from the one end 10a of the coil 20 by a desired amount (for example, 20 mm) when irradiating the magnetic flux to the irradiation target 41 located at the bottom of the irradiation object 40 having a concave shape (in other words, below the surface of the irradiation object 40), when the one end 21a of the magnetic core 21 is disposed to face the irradiation target 41.

In certain cases, as illustrated in FIG. 4, the coil 20 may physically interfere with the structure around the irradiation target 41, and it may not possible to bring the one end 20a of the coil 20 sufficiently closer to the irradiation target 41 (for example, up to the position of 5 mm from the irradiation target 41). In one aspect, where the one end 21a of the magnetic core 21 has been adjusted to axially project from the one end 20a of the coil 20 by a desired amount, the one end 21a can be positioned to be sufficiently close to the irradiation target 41 (for example, up to the position of 5 mm from the irradiation target 31), without physically interfering with the structure around the irradiation target 41.

The alternating current may be supplied to the coil 20 from a power source (not illustrated) at a predetermined frequency (for example, 100 kHz). Alternating magnetic flux parallel to the axial direction may be formed on the magnetic core 21 inserted inside the coil 20. The alternating magnetic flux may be irradiated toward the irradiation target 41 from the one end 21a of the magnetic core 21.

In one aspect, for a magnetic core 21 as shown by example in FIG. 2, magnetic flux formed inside the magnetic core 21 may be emitted in the axial direction from the one end 21a of the magnetic core 21, after being kept in a state of being parallel to the axial direction, over a long distance by which the one end 21a of the magnetic core 21 protrudes with respect to the one end 20a of the coil 20 (in other words, the magnetic flux may flow down the length of the magnetic core 21 to the one end 21a that protrudes from coil 20). As a result, in some instances, the one end 21a of the magnetic core 21 may be positioned to be sufficiently close to the irradiation target 41 even if it is not possible to bring the one end 20a of the coil 20 sufficiently closer to the irradiation target 41. Thus, the irradiation target 41 may be effectively irradiated with the magnetic flux, for example, at the magnetic flux density of 10 mT. In one aspect, magneto-sensitive heating particles may be provided to the irradiation target 31 prior to irradiation. In some cases, the magneto-sensitive heating particles in the irradiation target 31 may be magnetically heated by the magnetic flux, and the irradiation target 31 heated by the heat generation of the magneto-sensitive heating element when exposed to the magnetic flux.

In another aspect, the relative position of the magnetic core 21 with respect to the coil 20 may be adjusted so that the one end 21a of the magnetic core 21 recedes axially inwards from the one end 20a of the coil 20 such that a recess is formed within the one end 20a of the coil 20. Magnetic flux formed within the recess may have increased magnetic flux density as compared to when the one end 21a of the magnetic core 21 is on the same plane as the one end 20a of the coil 10 or when the one end 21a of the magnetic core 21 protrudes axially outwards from the one end 20a of the coil 20.

According to the above-described example, when the magnetic core 21 is within inside the coil 20, the relative position of the magnetic core 21 with respect to the coil 20 in the axial direction of the coil 20 may be adjusted by a desired amount and the diffusion start position of the magnetic flux irradiated from the one end 21a of the magnetic core 21 may be adjusted by a desired amount in the axial direction of the coil 20. Thus, it is possible to easily change the irradiation pattern of the magnetic flux, depending on the relative position of the magnetic flux irradiation device 20 with respect to the irradiation target 31 or 41.

In addition, in the example devices shown in FIGS. 1 to 4, the magnetic core 21 has a quadrangular prism shape, but is not limited thereto, and the magnetic core 21 may have a cylindrical shape or a prismatic shape such as an N prism shape (N is a natural number of 3 or 5 or higher).

In some cases, the screw threadings 20s and 21h corresponding to each other are provided on the inner peripheral surface of the coil housing 20h and the outer peripheral surface of the magnetic core housing 21h, and by the action of the screw, the relative position of the magnetic core 21 with respect to the coil 20 is adjusted in the axial direction, but is not limited thereto, for example, a rack and pinion structure corresponding to each other may be provided on the inner peripheral surface of the coil housing 20h and the outer peripheral surface of the magnetic core housing 21h, and by the action of the rack and pinion, the relative position of the magnetic core 21 with respect to the coil 20 may be adjustable in the axial direction. In addition, as discussed above, other mechanisms for adjusting the position of the magnetic core may also be used.

A second example will be described with reference to FIGS. 5(a), 5(b), and 6. FIG. 5(a) is a schematic side cross-sectional view illustrating a magnetic flux irradiation device according to the second example, and FIG. 5(b) is a schematic internal plan view thereof. FIG. 6 is a schematic side cross-sectional view illustrating a state in which the relative position of the magnetic core 21 with respect to the coil 20 in the axial direction of the coil 20 is adjusted by a desired amount in the magnetic flux irradiation device of FIG. 5(a).

Figure 6:
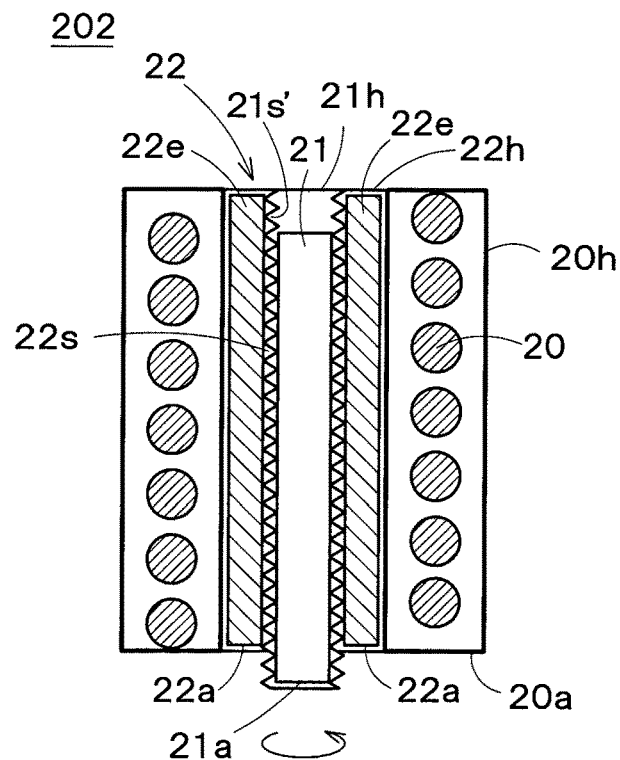
FIG. 6 is a schematic side cross-sectional view illustrating a state in which the relative position of the magnetic core with respect to the coil in the axial direction of the coil is adjusted by a desired amount in the magnetic flux irradiation device of FIG. 5(a).

In one aspect, as illustrated in FIGS. 5 (a) and 5 (b), a magnetic flux irradiation device 202 may also have an auxiliary magnetic core 22 inserted inside the coil 20 parallel to the axis of the coil 20 and configured to receive the magnetic core 21 in a central cavity defined within the auxiliary magnetic core 22, in addition to the components discussed above with respect to the magnetic flux irradiation device 201 according to the first example.

In some instances, as illustrated in FIG. 5(b), the auxiliary magnetic core 22 may have six columnar portion auxiliary magnetic core elements 22e that are uniformly disposed circumferentially within a central cavity defined within coil 20. In one example, each of the auxiliary magnetic core elements 22e may have a cylindrical shape having a diameter of 15 mm and an axial length of 120 mm. The material of each auxiliary magnetic core element 22e may be, for example, a Mn—Zn ferrite material. In some cases, as illustrated in FIG. 5(b), the auxiliary magnetic core elements 22e adjacent to each other are disposed to be spaced apart from each other. However, in other cases, the auxiliary magnetic core elements 22e may be disposed to abut against each other. In some instances, when the number of magnetic core elements increases and the magnetic core cross-sectional area increases, the magnetic flux density emitted from the magnetic core 22 may be distributed (decline). As discussed above, magnetic core elements 22 may have other sizes and or be made of other materials.

In one instance, as illustrated in FIG. 5(a), the one end 22a of the auxiliary magnetic core 22 may be configured to be positioned on the same plane as the one end 20a of the coil 20.

In one aspect, as illustrated in FIGS. 5(a) and 6, the auxiliary magnetic core 22 may be housed within the auxiliary magnetic core housing 22h having a cavity on the inner peripheral side configured to receive the magnetic core 21 housed within the magnetic core housing 21h. In some cases, the magnetic core housing 21h may be made of resin containing a magnetic material (for example, polyethylene resin mixed with ferrite). In some cases, at least a region including the inner peripheral surface of the auxiliary magnetic core housing 22h may be made of resin containing a magnetic material (for example, polyethylene resin mixed with ferrite). Thus, the simple magnetic coupling between the auxiliary magnetic core 22 and the magnetic core 21 is improved. However, in some aspects, the magnetic core 21 of the device 202 may not be housed in the magnetic core housing 21h.

In some instances, as illustrated in FIGS. 5(a) and 6, auxiliary magnetic core side screw threading 22s may be formed on the inner circumferential surface of the auxiliary magnetic core housing 22h. In some instances, magnetic core side screw threading 21s corresponding to the auxiliary magnetic core side screw 22s may be formed on the outer peripheral surface of the magnetic core housing 21h. In some instances, where the device 202 does not include a magnetic core housing 21h, the magnetic core side screw 21s may be formed on the outer peripheral surface of the magnetic core 21. In some cases, when the auxiliary magnetic core housing 22h and the magnetic core housing 21h or magnetic core 21 are relatively rotated about the axis of the coil 20, by the action of the screw threading, the relative position of the magnetic core 21 housed within the magnetic core housing 21h or magnetic core 21 with respect to the auxiliary magnetic core 22 housed within the auxiliary magnetic core housing 22h may be easily adjusted by a desired amount in the axial direction of the coil 20.

In one aspect, the auxiliary magnetic core housing 22h may be fixed to the coil housing 20h when positioned within the cavity of the coil housing 20h, and the auxiliary magnetic core 22 housed within the auxiliary magnetic core housing 22h may be stationary with respect to the coil 20 housed within the coil housing 20h. In some instances, the relative position of the magnetic core 21 with respect to the coil 20 and with respect to the auxiliary magnetic core 22 may be adjusted by a desired amount in the axial direction of the coil 20.

Other configurations are substantially the same as those of the first example illustrated in FIGS. 1 and 2. In FIGS. 5(a), 5(b), and 6, the same parts as those of the first example illustrated in FIGS. 1 and 2 are denoted by the same reference numerals, and a detailed description thereof will not be provided.

In one aspect, for a device such as the magnetic flux irradiation device 201 as described above, when the alternating current is supplied to the coil 20 from a power source (not illustrated) at a predetermined frequency, alternating magnetic flux parallel to the axial direction may be formed on the magnetic core 21 and on the auxiliary magnetic core 22 that are positioned within the coil 20, respectively.

In one aspect, as illustrated in FIG. 5(a), the relative position of the magnetic core 21 with respect to the coil 20 may be adjusted so that the one end of the magnetic core 21 is placed on the same plane as the one end of the auxiliary magnetic core 22. Alternating magnetic flux may be formed on the magnetic core 21 and emitted axially outward from the one end 21a of the magnetic core 21, and the alternating magnetic flux formed on the auxiliary magnetic core 22 may be emitted axially outward from the one end 22a of the auxiliary magnetic core 22.

In another aspect, as illustrated in FIG. 6, the relative position of the magnetic core 21 with respect to the coil 20 may be adjusted so that the one end 21a of the magnetic core 21 projects axially outward from the one end 22a of the auxiliary magnetic core 22. Alternating magnetic flux formed on the auxiliary magnetic core 22 may be focused by the protruding of the magnetic core 21, and then may be emitted axially outward from the one end 21a of the magnetic core 21, together with the alternating magnetic flux formed on the magnetic core 21.

In another aspect, the relative position of the magnetic core 21 with respect to the coil 20 may be adjusted so that the one end 21a of the magnetic core 21 recedes axially inwards from the one end 22a of the auxiliary magnetic core 22 such that a recess is formed within the one end of the auxiliary magnetic core 22. Magnetic flux formed within the recess may have increased magnetic flux density as compared to when the one end 21a of the magnetic core 21 is on the same plane as the one end 22a of the auxiliary magnetic core 22 or when the one end 21a of the magnetic core 21 protrudes axially outwards from the one end 22a of the auxiliary magnetic core 22.

In some instances, according to the above-described second example, in addition to the same advantageous effects as those in the first example, when the one end 21a of the magnetic core 21 protrudes axially outward from the one end 22a of the auxiliary magnetic core 22, the magnetic flux formed on the auxiliary magnetic core 22 may be released after being focused by the protruding of the magnetic core 21, and the magnetic flux density may be further enhanced as compared to the first example.

In some cases, where the magnetic core housing 21h is made of resin containing a magnetic material, and at least the region including the inner peripheral surface of the auxiliary magnetic core housing is also made of resin containing a magnetic material, the magnetic coupling between the auxiliary magnetic core 22 and the magnetic core 21 may be improved, and it may be possible to further enhance the focusing effect of the magnetic flux from the auxiliary magnetic core 22 to the magnetic core 21.

In some cases, as in this example, the number of the auxiliary magnetic core elements 22e may be six, but is not limited thereto. In other cases, the number the auxiliary magnetic core elements 22e may be two to five, and seven or more.

In some cases, as in this example, each auxiliary magnetic core element 22e may have a cylindrical shape, but is not limited thereto. In some cases, the auxiliary magnetic core elements 22e may have a prismatic shape.

In some cases, as in this example, the auxiliary magnetic core 22 may have a plurality of auxiliary magnetic core elements 22e uniformly disposed circumferentially within a central cavity defined by the coil 20, but is not limited thereto. In some cases, the auxiliary magnetic core 22 may have a cylindrical shape that surrounds the periphery of the magnetic core 21 within the coil 20.

In some cases, as in this example, the screw threadings 22s and 21h corresponding to each other may be provided on the inner peripheral surface of the auxiliary magnetic core housing 22h and the outer peripheral surface of the magnetic core housing 21h, and by the action of the screw threading, the relative position of the magnetic core 21 with respect to the auxiliary magnetic core 22 may be adjustable in the axial direction, but is not limited thereto. For example, in other cases, rack and pinion structures corresponding to each other may be provided on the inner peripheral surface of the auxiliary magnetic core housing 22h or auxiliary magnetic core 22 and the outer peripheral surface of the magnetic core housing 21h or magnetic core 21, and by the action of the rack and the pinion, the relative position of the magnetic core 21 with respect to the auxiliary magnetic core 22 may be adjustable in the axial direction. In addition, as discussed above, in other cases, other mechanisms for adjusting the position of the magnetic core may also be used.

Figure 19:
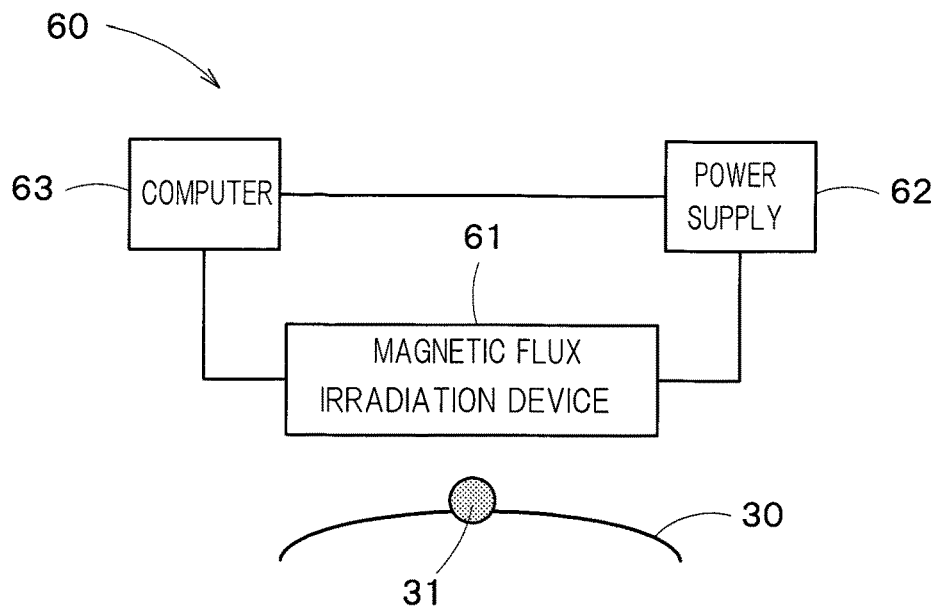
FIG. 19 is a schematic of a system including a magnetic flux irradiation device according to various examples.

FIG. 19 is a block diagram illustrating systems for using the magnetic flux irradiation devices described in detail in Section I. For example, the system 60 includes a magnetic flux irradiation device 61 having a coil 10 and an adjustable magnetic core disposed within a central cavity of the coil 10. The device 61 can be any of the example devices described previously in Section I and any variations thereof as within the scope of this disclosure. The system 60 also includes a power supply 62 configured to supply electrical current to the coil 10 of the magnetic flux irradiation device 61. In some instances, the power supply 62 is configured to supply alternating current to the coil 10. The system 60 also includes a computer 63 configured to perform at least one of control operation of the magnetic flux irradiation device 61 or process data obtained from monitoring an irradiation target 31 upon which the magnetic flux irradiation device 61 is used. While irradiation target 31 is used for illustrative purposes in FIG. 19, alternatively, irradiation target 41 may also be irradiated using system 60.

In one aspect, the position of the magnetic core with respect to the coil (and the auxiliary magnetic core, if present) is adjusted based on, for example, characteristics of the irradiation target to be irradiated or the magnetic flux density desired. The position of the first end of the magnetic core may be adjusted to be on the same plane as the first end of the coil or to position the magnetic core to recede axially inwards or protrude axially outwards in relation to the coil by a desired about. The position of the magnetic core may be adjusted manually, for example, by twisting the magnetic core within the device if the magnetic core or magnetic core housing has screw threading formed thereon and the coil housing or auxiliary core housing or auxiliary core has matching screw threading formed thereon. As discussed above, other mechanisms of moving the position of the magnetic core in relation to the position of the coil are also contemplated.

In one aspect, when the power supply 62 is activated and supplies alternating current to the coil 10, alternating magnetic flux is generated on the magnetic core. In one aspect, the alternating magnetic flux is emitted from the first end of the magnetic core and can irradiate an irradiation target 31 (such as a tumor) of an irradiation object 30 (such a subject with a tumor) that is positioned to face the first end of the magnetic core.

In some instances, the computer 63 may be configured to control the power supply 62. In other instances, the computer 63 may be configured to monitor the alternating current supplied to the coil 10 by the power supply 62. In some cases, the computer 63 may be configured to receive and process data about the irradiation object 30 or the irradiation target 31. For example, the computer 63 may be configured to process visual or temperature data obtained from monitoring the irradiation target 31. In another example, the computer 63 may be configured to adjust the position of the magnetic core with respect to the coil (and the auxiliary magnetic core, if present), such as by adjusting the position of the first end of the magnetic core to be on the same plane as the first end of the coil or to position the magnetic core to recede axially inwards or protrude axially outwards in relation to the coil by a desired about. In some instances, the computer 63 is configured to perform more than one of the functions described in this paragraph or one of the described functions and some other function relating to use of the device 61.

The computer 63 may be a variety of different computing devices for storing and processing data. The computer 63 may comprise, for example, a smartphone, tablet, e-reader, laptop computer, desktop computer, or a gaming device. In some embodiments, the computing device may comprise a processor interfaced with other hardware via a bus. A memory, which can include any suitable tangible (and non-transitory) computer-readable medium such as RAM, ROM, EEPROM, or the like, can embody program components that configure operation of the computer 63. The computing device may also comprise input/output interface components (for example, a display, keyboard, touch-sensitive surface, and mouse) and additional storage.

In some instances, the computer 63 may comprise a communication device. The communication device may comprise one or more of any components that facilitate a network connection. For example, the communication device may be wireless and may comprise wireless interfaces such as IEEE 802.11, Bluetooth, or radio interfaces for accessing cellular telephone networks (for example, transceiver/antenna for accessing a CDMA, GSM, UMTS, or other mobile communications network). In some cases, the communication device may be wired and may comprise interfaces such as Ethernet, USB, or IEEE 1394.

The system 60 may include additional computers each of which perform distinct functions such as those described above or other functions useful to the use of the system 60 to irradiate an irradiation target 31.

Figure 20:
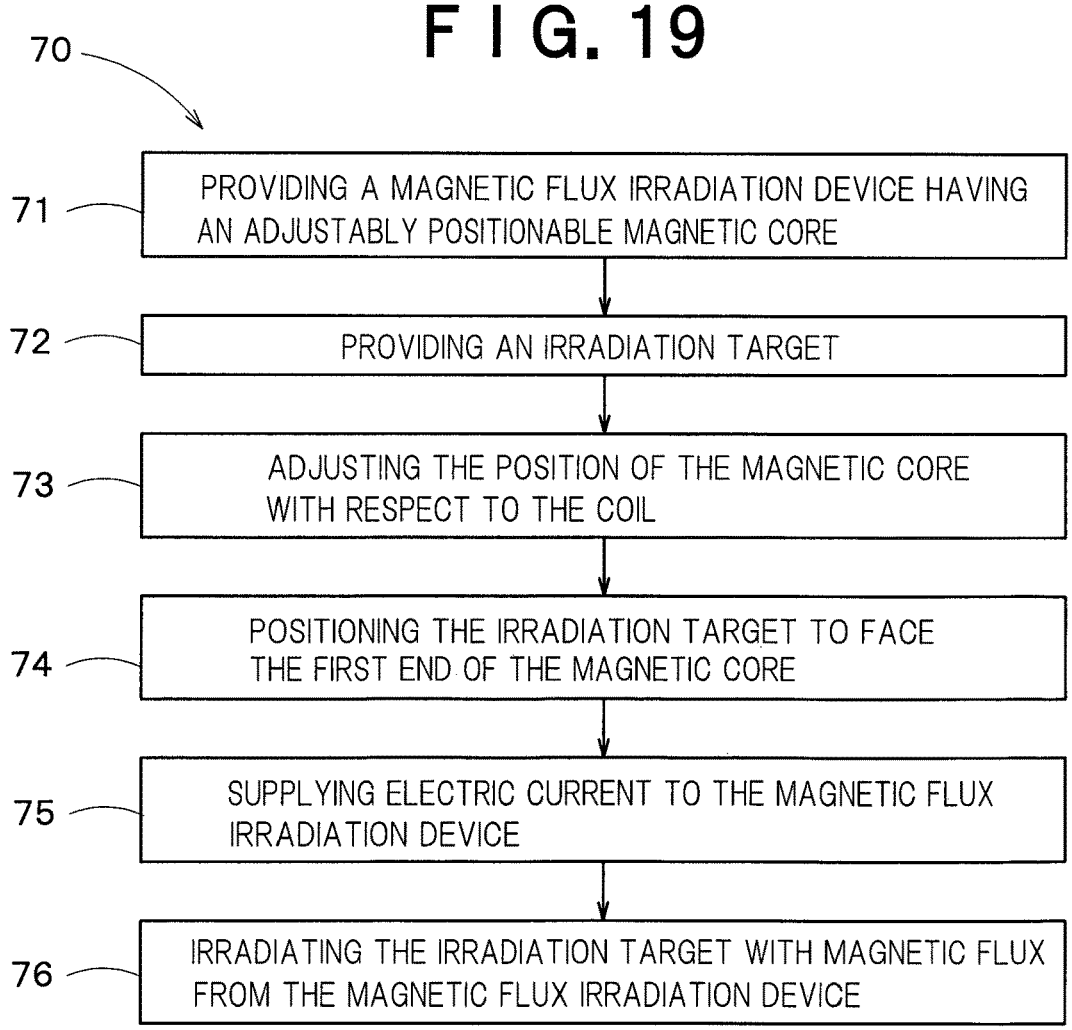
FIG. 20 is a block diagram of a method of irradiating an irradiation target of an irradiation object using a magnetic flux irradiation device according to various examples.

FIG. 20 is a block diagram illustrating methods for using the magnetic flux irradiation devices described in detail in Section I. In one aspect, the method 70 is a method of irradiating an irradiation target with magnetic flux. Methods of irradiating an irradiation target with magnetic flux as described herein may be useful for treating a subject with a tumor.

In block 71, a magnetic flux irradiation device having an adjustably positionable magnetic core is provided. The magnetic flux irradiation device may be one of the devices specifically described in the examples provided in Section I of this disclosure or may be variations thereof as within the scope of this disclosure. In block 72, an irradiation target is provided. In one aspect, the irradiation target is on the surface of or within an irradiation object. For example, the irradiation target may be a tumor of an irradiation subject.

In block 73, the position of the magnetic core with respect to the coil is adjusted, for example, based on characteristics of the irradiation target to be irradiated or the magnetic flux density desired. As described above, the adjustment of the magnetic core with respect to the coil may be performed manually or may be automated through use of a computer and other components. Various mechanisms of adjusting the position of the magnetic core may be used, as described above.

In block 74, the irradiation target is positioned to face the first end of the magnetic core. In one aspect, the irradiation target may be positioned within a certain proximity of the first end of the magnetic core. For example, the irradiation target may be positioned from about 5 mm to about 15 cm below the first end of the magnetic core. For example, the irradiation target may be positioned at a distance of about 5 mm, 10 mm, 20 mm, 30 mm, 50 mm, 100 mm, or some other distance up to about 15 cm from the first end of the magnetic core. Where the irradiation target is inserted within the magnetic core, it may be positioned to not be in contact with the magnetic core or any other part of the device. In one aspect, the position to which the magnetic core is adjusted in the method 70 may be based on the nature of the irradiation target to be irradiated. For example, the irradiation target may be on the surface of the irradiation object or just below the surface of the irradiation object, and the surface of the irradiation object may be relatively flat or may be convex. In this instance, the first end of the magnetic core may be adjusted to be on the same plane as the first end of the coil. Alternatively, the first end of the magnetic core may be adjusted to be recessed axially with respect to the first end of the coil. In another example, the irradiation target may be on the surface of the irradiation object or just below the surface of the irradiation object but the structure of the irradiation object may obstruct access to the irradiation target. In this instance, the first end of the magnetic core may be adjusted to protrude axially with respect to the first end of the coil may be provided.

In block 75, electric current is supplied to magnetic flux irradiation device. In block 76, the irradiation target is irradiated with magnetic flux. In one aspect, the irradiation target can be irradiated with magnetic flux when electrical current is supplied to the coil (such as from a power supply) to generate magnetic flux on the magnetic core that is emitted from the first end of the magnetic core and irradiated to the irradiation target. In another aspect, the irradiation target may be positioned in sufficient proximity to the first end of the magnetic core so as to receive a desired magnetic flux density. In one aspect, the irradiation target is irradiated with a magnetic flux density of about 0.5 mT to about 30 mT. For instance, the magnetic flux density can be about 5 mT, about 10 mT, about 15 mT, about 20 mT, about 25 mT, or about 30 mT, or other numbers within this range.

In some instances, magneto-sensitive heating particles may be provided to the irradiation target prior to irradiation. In some instances, the irradiation target may contain a magneto-sensitive heating particles that heat when exposed to magnetic flux. In one aspect, the magneto-sensitive heating particles may be injected into the irradiation target. For example, the magneto-sensitive heating particles in the irradiation target may be magnetically heated by the magnetic flux, and the irradiation target heated by the heat generation of the magneto-sensitive heating element when exposed to the magnetic flux. In one example, magneto-sensitive heating particles can include magnetite particles. In another example, the magneto-sensitive heating particles may be magnetic cationic liposomes. However, a range of materials can be used to prepare magneto-sensitive heating particles and this disclosure is not limited to those described.

II. Magnetic Flux Irradiation Device Having a Replaceable Magnetic Core

In one aspect, in the below-described third to seventh examples, two magnetic cores capable of being detachably inserted inside the coil 10 are provided with respect to one coil 10, but the number of the magnetic cores is not limited thereto. For example, three, four, five, or more magnetic cores may be provided. In one aspect, any combination of different magnetic cores can be provided in the context of the magnetic flux irradiation device. For example, the magnetic core that is inserted into the device can be selected from any of the below-described first to fifth magnetic cores 11 to 15.

Figure 7:
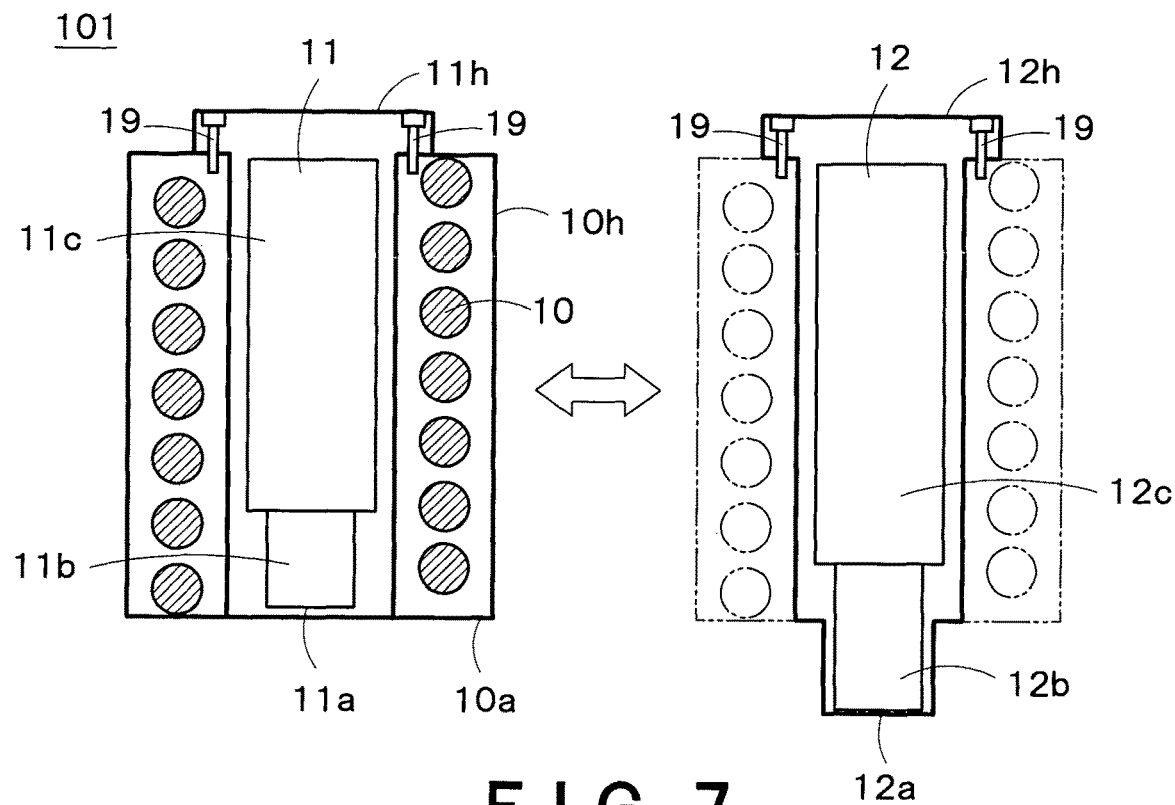
FIG. 7 is a schematic side cross-sectional view illustrating a magnetic flux irradiation device according to a third example.
Figure 8:
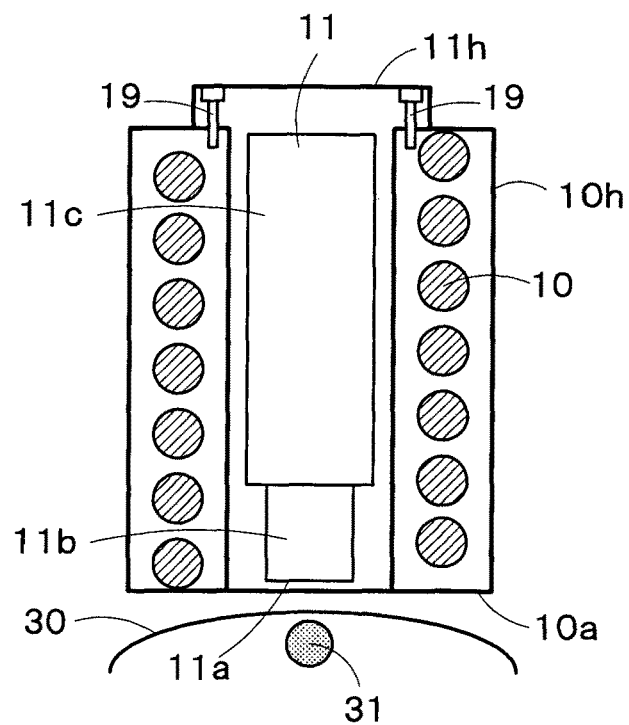
FIG. 8 is a diagram for illustrating an aspect in which magnetic flux is irradiated from a first magnetic core in the magnetic flux irradiation device of FIG. 7.
Figure 9:
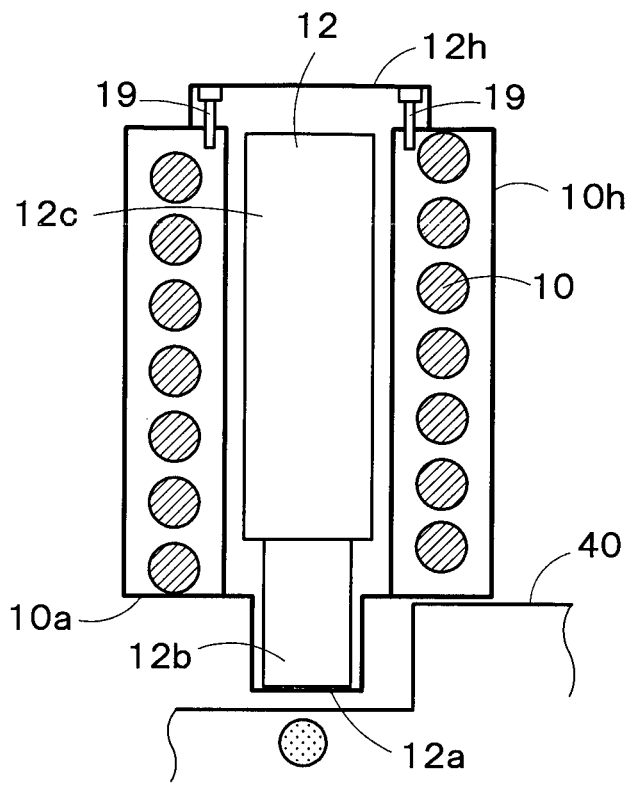
FIG. 9 is a diagram for illustrating an aspect in which magnetic flux is irradiated from a second magnetic core in the magnetic flux irradiation device of FIG. 7.

A third example will be described with reference to FIGS. 7 to 9. FIG. 7 is a schematic side cross-sectional view illustrating a magnetic flux irradiation device according to a third example. FIG. 8 is a diagram for illustrating an aspect in which magnetic flux is irradiated from the first magnetic core in the magnetic flux irradiation device of FIG. 7. FIG. 9 is a diagram for illustrating an aspect in which magnetic flux is irradiated from the second magnetic core in the magnetic flux irradiation device of FIG. 7.

In one aspect, as illustrated in FIG. 7, a magnetic flux irradiation device 101 according may have a cylindrical coil 10, and a first magnetic core 11 that is detachably inserted inside the coil 10 to be parallel to the axis of the coil 10.

As illustrated in FIG. 7, the coil 10 may be a solenoid coil having a cylindrical shape. In one example, a diameter of the coil 10 may be 70 mm, and an axial length of the coil 10 may be 120 mm.

In one aspect, as illustrated in FIG. 7, the first magnetic core 11 may have a columnar portion 11b of a small cross-sectional area that defines one end 11a, and a columnar portion 11c of a large cross-sectional area that is axially and coaxially adjacent to the columnar portion 11b of the small cross-sectional area. For example, the columnar portion 11b of the small cross-sectional area may have a cylindrical shape. In another example, the columnar portion 11c of the large cross-sectional area may have a cylindrical shape. For example, the columnar portion 11b of the small cross-sectional area may have a diameter of 20 mm and an axial length of 20 mm. For example, the columnar portion 11c of the large cross-sectional area may have a diameter of 50 mm and an axial length of 100 mm. A material of the first magnetic core 11 may be, for example, a Mn—Zn ferrite material. As discussed above, magnetic core 11 may have other sizes and or be made of other materials.

In one example, as in this example, the one end 11a of the first magnetic core 11 may be adapted to be positioned on the same plane as the one end 10a of the coil 10. In this disclosure, "the same plane as the one end 10a of the coil 10" includes a plane located within 1 mm axially inward from the one end 10a of the coil 10.

A power source (not illustrated) may be electrically connected to the coil 10. When the alternating current is supplied to the coil 10 from the power source at a predetermined frequency (for example, 50 kHz to 400 kHz), alternating magnetic flux parallel to the axial direction may be formed on the first magnetic core 11 positioned within the coil 10. In one aspect, the alternating magnetic flux may be emitted from the one end 11a of the first magnetic core 11 in a first pattern (magnetic flux density) in the axial direction, after being focused at the columnar portion 11b of the small cross-sectional area.

In one aspect, as shown in this example, the first magnetic core 11 is configured to be fixed to the coil 10 using the screw 19 made of a nonconductive material when the first magnetic core 11 is positioned within a central cavity defined by the coil 10. However, as discussed above, other mechanisms of fixing the magnetic core 11 to the coil 10 may be used instead.

In some instances, as illustrated in FIG. 7, the coil 10 may be coaxially housed within the coil housing 10h having a cavity on the inner peripheral side, and the first magnetic core 11 may be coaxially housed within the first magnetic core housing 11h that is configured to be positioned within the cavity. In some cases, a flange extending radially outward from the cavity of the coil housing 10h may be provided at the other end of the first magnetic core housing 11h. When the flange is in close contact with the other end of the coil housing 10h, the screw 19 made of nonconductive material may be passed through the flange and inserted into a screw hole provided in the coil housing 10h. In one aspect, the relative position of the first magnetic core 11 with respect to the coil 10 is kept at a predetermined position (fixed) when the first magnetic core 11 is inserted inside the coil 10. In some cases, because the screw 19 (or other mechanism of fixing the position of the magnetic core 11 with respect to the coil 10) is made of a nonconductive material, the screw 19 may not be inductively heated by the alternating magnetic field formed by the coil 10.

In one aspect, as illustrated in FIG. 7, a second magnetic core 12 that can be detachably inserted inside the coil 10 to be parallel to the axis of the coil 10 may be positioned within the central cavity defined within the coil 10 after the first magnetic core 11 is removed from the interior of the coil 10.

In one instance, as illustrated in FIG. 7, the second magnetic core 12 may have a columnar portion 12b of a small cross-sectional area that defines one end 12a, and a columnar portion 12c of a large cross-sectional area that is axially and coaxially adjacent to the columnar portion 12b of the small cross-sectional area. In one aspect, the shape of the columnar portion 12b of the small cross-sectional area and the columnar portion 12c of the large cross-sectional area may be as described with respect to the shape of the columnar portion 11b of the small cross-sectional area and the columnar portion 11c of the large cross-sectional area of magnetic core 11. In one aspect, the dimensions of the columnar portion 12b of the small cross-sectional area and the columnar portion 12c of the large cross-sectional area may be as described with respect to the shape of the columnar portion 11b of the small cross-sectional area and the columnar portion 11c of the large cross-sectional area of magnetic core 11. In one aspect, the material of the magnetic core 12 may be as described with respect to magnetic core 11. For example, the columnar portion 12b of the small cross-sectional area may have a cylindrical shape having a diameter of 20 mm and an axial length of 70 mm. For example, the columnar portion 12c of the large cross-sectional area may have a cylindrical shape having a diameter of 50 mm and an axial length of 100 mm. The material of the second magnetic core 12 may be, for example, a Mn—Zn ferrite material.

In one instance, as illustrated in FIG. 7, the columnar portion 12b of the small cross-sectional area of the second magnetic core 12 may be adapted to protrude axially outward from the one end 10a of the coil 10 when the second magnetic core 12 is positioned within the coil 10 and parallel to the axis of the coil 10. The amount of protrusion of the columnar portion 12b of the small cross-sectional area of the second magnetic core 12 with respect to the one end 10a of the coil 10 may vary based on the desired magnetic flux density to be emitted from the magnetic core 12. For example, the columnar portion 12b of the small cross-sectional area of the second magnetic core 12 may protrude with respect to the one end 10a of the coil 10 by about 20 mm. In some instances, the amount of protrusion may be from about 5 mm to about 50 mm or about 10 mm to about 40 mm, or about 15 mm to about 30 mm.

When the alternating current is supplied to the coil 10 from the power source at a predetermined frequency, when the second magnetic core 12 is inserted inside the coil 10, the alternating magnetic flux parallel to the axial direction may be formed on the second magnetic core 12 and may be emitted from the one end 12a of the second magnetic core in a second pattern (magnetic flux density) in the axial direction, after being focused at the columnar portion 12b of the small cross-sectional area.

In one aspect, the magnetic flux formed on the second magnetic core 12 can be emitted in the axial direction from the one end 12a of the second magnetic core 12, after being kept in a state of being parallel to the axial direction, over a long distance by which the columnar portion 12*b* of the small cross-sectional area of the second magnetic core 12 protrudes with respect to the one end 10*a* of the coil 10. For that reason, when the second magnetic core 12 is inserted inside the coil 10, the diffusion start position of magnetic flux emitted from the one end of the magnetic core can be extended, as compared to when the first magnetic core 11 is inserted inside the coil 10.

In some instances, the amount of protrusion of the columnar portion 12*b* of the small cross-sectional area of the second magnetic core 12 with respect to the one end 10*a* of the coil 10 may be 50 mm or less. In some instances, when the amount of protrusion is higher than 50 mm, the magnetic flux formed inside the second magnetic core 12 may escape outward from the side surface of the columnar portion 12*b* of the small cross-sectional area, and the density of the magnetic flux emitted from the one end 12*a* may be decreased.

In one aspect, as discussed above with respect to the third example, the second magnetic core 12 may be adapted to be fixed to the coil 10. In some cases, as illustrated in FIG. 7, the screw 19 made of nonconductive material may be used to detachably connect the second magnetic core 12 to the coil 10. In other cases, other mechanisms of detachably connecting the first magnetic core 11 and the second magnetic core 12 may be used.

In some instances, as illustrated in FIG. 7, the second magnetic core 12 may be coaxially housed within the second magnetic core housing 12*h* that is capable of being inserted inside the cavity of the coil housing 10*h*. In some cases, at the other end of the second magnetic core housing 12*h*, a flange extending radially outward from the cavity of the coil housing 10*h* may be provided. When the flange is in close contact with the other end of the coil housing 10*h*, the screw 19 may be passed through the flange and fitted into the screw hole provided in the coil housing 10*h*. Thus, the relative position of the second magnetic core 12 with respect to the coil 10 kept at a predetermined position when the second magnetic core 12 is inserted inside the coil 10.

Next, the operation of the above-described example will be described.

In one instance, as illustrated in FIG. 8, the irradiation target 31 may be located inside the irradiation object 30 having a convex shape. In some cases, when the first magnetic core 11 is inserted inside the coil 10 to be parallel to the axis of the coil 10, the one end 11*a* of the first magnetic core 11 may be disposed to face the irradiation target 31. The one end 11*a* of the first magnetic core 11 may be positioned to be sufficiently close to the irradiation target 31 (for example, up to the position of 5 mm from the irradiation target 31).

In one instance, alternating current may be supplied to the coil 10 from a power source (not illustrated) at a predetermined frequency (for example, 50 to 400 kHz, such as 100 kHz). Alternating magnetic flux parallel to the axial direction may be formed on the first magnetic core 11 inserted inside the coil 10, and the alternating magnetic flux may be irradiated to the irradiation target 31 from the one end 11*a* of the first magnetic core 11 in the first pattern, after being focused at the columnar portion 11*b* of the small diameter. In some cases, the one end 11*a* of the first magnetic core 11 may be positioned to be sufficiently close to the irradiation target 31, and the irradiation target 31 may be effectively irradiated with the magnetic flux. In some instances, the magnetic flux density may be about 0.5 mT to about 30 mT. For example, the magnetic flux density may be about 20 mT. In one aspect, magneto-sensitive heating particles may be provided to the irradiation target 31 prior to irradiation. In this aspect, the magneto-sensitive heating particles in the irradiation target 31 may be magnetically heated by the magnetic flux, and the irradiation target 31 heated by the heat generation of the magneto-sensitive heating element when exposed to the magnetic flux.

In some cases, as illustrated in FIG. 9, the irradiation target 41 may be located at the bottom of the irradiation object 40 having a concave shape. Instead of the first magnetic core 11, the second magnetic core 12 may be inserted into the device 101. For example, if the first magnetic core 11 is inserted in the device 101, the screw 19 may be removed from the first magnetic core housing 11*h* and the coil housing 10*h* and the first magnetic core 11 may be removed from the interior of the coil 10. The second magnetic core 12 may then be inserted inside the coil 10 to be parallel to the axis of the coil 10, and the second magnetic core housing 12*h* is fixed to the coil housing 10*h* using the screw 19 made of resin. In some examples, the first magnetic core 11 and the second magnetic core 12 may not be housed in magnetic core housings 11*h* or 12*h* and may be detachably connected to the coil 10 via different mechanisms, as discussed above.

In one instance, as shown in this example; the one end 12*a* of the second magnetic core 12 inserted inside the coil 10 may be disposed to face the irradiation target 41. In some cases, as illustrated in FIG. 9, the coil 10 may physically interfere with the structure around the irradiation target 41, and it may not be possible to bring the one end 10*a* of the coil 10 sufficiently close to the irradiation target 41 (for example, up to the position of 5 mm from the irradiation target 41). However, because the columnar portion 12*b* of the small cross-sectional area of the second magnetic core 12 has a smaller diameter than the one end 10*a* of the coil 10 and protrudes axially from the end 10*a*, around the irradiation target 41, the columnar portion 12*b* can be positioned to be sufficiently (for example, up to the position of 5 mm from the irradiation target 31) close to the irradiation target 41, without physically interfering with the structure around the irradiation target 41.

In one aspect, when the alternating current is supplied to the coil. 10 from a power source (not illustrated) at a predetermined frequency (for example, 50 kHz to 40 kHz, such as 100 kHz), alternating magnetic flux parallel to the axial direction may be formed on the second magnetic core 12 inserted inside the coil 10, and the alternating magnetic flux may be irradiated to the irradiation target 41 from the one end 12*a* of the second magnetic core 12 in a second pattern (magnetic flux density), after being focused at the columnar portion 12*b* of the small cross-sectional area.

In some instances, as illustrated in FIGS. 7 and 9, the magnetic flux formed inside the second magnetic core 12 may be emitted in the axial direction from the one end 12*a* of the second magnetic core 12, after being kept in a state of being parallel to the axial direction, over a long distance by which the columnar portion 12*b* of the small cross-sectional area of the second magnetic core 12 protrudes with respect to the one end 10*a* of the coil 10. In certain cases, even if it is not possible to bring the one end 10*a* of the coil 10 sufficiently closer to the irradiation target 41, because the one end 12*a* of the second magnetic core 12 may be positioned to be sufficiently close to the irradiation target 41, the irradiation target 41 may be effectively irradiated with the magnetic flux. For example, the magnetic flux density emitted from the one end 12*a* of the second magnetic core may be about 0.5 mT to about 30 mT. For example, the magnetic flux density may be about 10 mT. In one aspect, magneto-sensitive heating particles may be provided to the irradiation target 31 or 41 prior to irradiation. In this aspect, the magneto-sensitive heating particles in the irradiation target 31 or 41 may be magnetically heated by the magnetic flux, and the irradiation target 31 or 41 heated by the heat generation of the magneto-sensitive heating element when exposed to the magnetic flux.

Thus, in one aspect, according to the above-described example, because the second magnetic core 12 may be inserted inside the coil 10 once the first magnetic core 11 has been removed from the interior of the coil 10, it is possible to easily change the irradiation pattern of the magnetic flux from the first pattern to the second pattern, depending on the relative position of the magnetic flux irradiation device 101 with respect to the irradiation target 31 or 41.

Further, according to this example, when the second magnetic core 12 is inserted inside the coil 10, the magnetic flux formed inside the second magnetic core 12 can be emitted axially from the one end 12a of the second magnetic core 12, after being kept in a state of being parallel to the axial direction, over a long distance by which the columnar portion 12b of the small cross-sectional area of the second magnetic core 12 protrudes with respect to the one end 10a of the coil 10. For that reason, since the second magnetic core 12 is inserted inside the coil 10 in place of the first magnetic core 11, the diffusion start position of the magnetic flux irradiated from the one end of the magnetic core can be extended, and it is possible to effectively irradiate the magnetic flux, even to the irradiation target 41 to which the one end 11a of the first magnetic core 11 cannot be brought sufficiently closer.

In addition, in this example, the columnar portion 11b of the small cross-sectional area and the columnar portion 11c of the large cross-sectional area of the first magnetic core 11 have a cylindrical shape, respectively, but are not limited thereto, and they may have a prismatic shape, respectively. Furthermore, the columnar portion 12b of the small cross-sectional area and the columnar portion 12c of the large cross-sectional area of the second magnetic core 12 have a cylindrical shape, respectively, but are not limited thereto, and they may have a prismatic shape, respectively.

Figure 10:
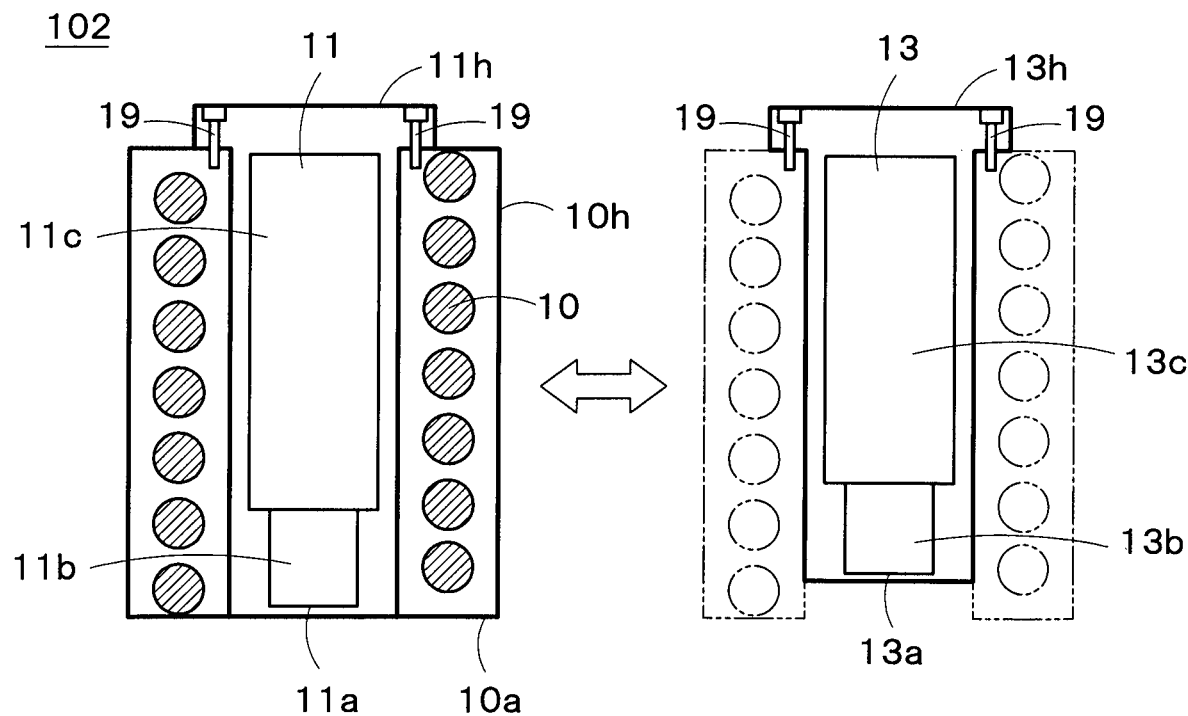
FIG. 10 is a schematic side cross-sectional view illustrating a magnetic flux irradiation device according to a fourth example.

A fourth example will be described referring to FIGS. 10 and 11. FIG. 10 is a schematic side cross-sectional view illustrating a magnetic flux irradiation device according to the fourth example. FIG. 11 is a diagram for illustrating an aspect in which the magnetic flux is irradiated from the third magnetic core in the magnetic flux irradiation device of FIG. 10.

In one aspect, as illustrated in FIG. 10, a magnetic flux irradiation device 102 according to the fourth example may have a third magnetic core 13 (the second magnetic core of claims 11 and 12) inserted within the coil 10 in place of the second magnetic core 12 (or the first magnetic core 11) of the magnetic flux irradiation device 101 according to the third example.

In one example, as illustrated in FIG. 10, the third magnetic core 13 may have a columnar portion 13b of a small cross-sectional area that defines one end 13a, and a columnar portion 13c of a large cross-sectional area that is coaxially adjacent to the axial direction of the columnar portion 13b of the small cross-sectional area. In one aspect, the shape of the columnar portion 13b of the small cross-sectional area and the columnar portion 13c of the large cross-sectional area may be as described with respect to the shape of the columnar portion 11b of the small cross-sectional area and the columnar portion 11c of the large, cross-sectional area of magnetic core 11. In one aspect, the dimensions of the columnar portion 13b of the small cross-sectional area and the columnar portion 13c of the large cross-sectional area may be as described with respect to the shape of the columnar portion 11b of the small cross-sectional area and the columnar portion 11c of the large cross-sectional area of magnetic core 11. In one aspect, the material of the magnetic core 13 may be as described with respect to magnetic core 11. For example, the columnar portion 13b of the small cross-sectional area has a cylindrical shape having a diameter of 20 mm and an axial length of 20 mm. Furthermore, for example, the columnar portion 13c of the large cross-sectional area may have a cylindrical shape having a diameter of 50 mm and an axial length of 90 mm. The material of the third magnetic core 13 may be, for example, a Mn—Zn ferrite material.

In one example, as illustrated in FIG. 10, when the third magnetic core 13 is inserted inside the coil 10 to be parallel to the axis of the coil 10, the one end 13a of the third magnetic core 13 is adapted to be recessed inside the one end 10a of the coil 10. The amount of recession of the one end 13a of the third magnetic core 13 with respect to the one end 10a of the coil 10 is, for example, 1 mm to 10 mm. In some cases, the amount of recession may up to 20 mm where the dimensions of the magnetic core 13 are greater, for example, than the specific example dimensions provided in the preceding paragraph.

In one aspect, where the third magnetic core 13 is inserted inside the coil 10, alternating current may be supplied to the coil 10 from the power source at a predetermined frequency. The alternating magnetic flux parallel to the axial direction may be formed on the third magnetic core 13 inserted inside the coil 10, and after being focused at the columnar portion 13b of the small diameter, the alternating magnetic flux may be irradiated in the axial direction from the one end 13a of the third magnetic core 13 in a third pattern (magnetic flux density).

In one aspect, the third magnetic core 13 may be adapted to be fixed to the coil 10 using the mechanisms described above (for example, screw 19 or another mechanism).

In some cases, as illustrated in FIG. 10, the third magnetic core 13 may be coaxially housed within the third magnetic core housing 13h capable of being inserted into the cavity of the coil housing 10h. In some instances, on the other end of the third magnetic core housing 13h, a flange extending radially outward from the cavity of the coil housing 10h may be provided, and when the flange is in close contact with the other end of the coil housing 10h, the screw 19 passing through the flange may be fitted into the screw hole provided in the coil housing 10h. Thus, where the third magnetic core 13 is inserted inside the coil 10, the relative position of the third magnetic core 13 with respect to the coil 10 may be kept at a predetermined position (fixed).

Other configurations are substantially the same as those of the third example illustrated in FIGS. 7 to 9. In FIGS. 10 and 11, the same parts as those of the third example illustrated in FIGS. 7 to 9 are denoted by the same reference numerals, and the detailed description thereof will not be provided.

Next, the operation of the above-described example will be described.

In some instances, as illustrated in FIG. 8, the irradiation target 31 may be located inside the irradiation object 30 having a convex shape.

In some instances, as illustrated in FIG. 11, the irradiation target 51 may protrude from the surface of an irradiation object 50 having a convex shape. In some cases, the third magnetic core 13 may be inserted into the device 102 after the first magnetic core 12 (or the second magnetic core 11)

is removed from the coil. For example, where the screw 19 is used to detachably connect the magnetic cores to the device 102, the screw 19 may be detached from the first magnetic core housing 11h and the coil housing 10h, after the first magnetic core 11 is removed from the interior of the coil 10, and the third magnetic core 13 may be inserted inside the coil 10 to be parallel to the axis of the coil 10, and then the third magnetic core housing 13h may be fixed to the coil housing 10h using the screw 19. In some instances, the one end 13a of the third magnetic core 13 may be receded axially inward from the one end 10a of the coil 10 thereby forming a recess a position that faces the one end 13a of the third magnetic core 13 within the coil 10.

In one aspect, the one end 13a of the third magnetic core 13 inserted inside the coil 10 may be disposed to face the irradiation target 51. For example, the irradiation target 51 can be positioned by being inserted within the recess formed at a position that faces the one end 13a of the third magnetic core 13 within the coil 10.

In one aspect, alternating current may be supplied to the coil 10 from a power source (not illustrated) at a predetermined frequency (for example, 50 kHz to 400 kHz, such as 100 kHz). Alternating magnetic flux parallel to the axial direction may be formed on the third magnetic core 13 inserted inside the coil 10, and after being focused at the columnar portion 13b of the small cross-sectional area, the alternating magnetic flux may be irradiated to the irradiation target 51 from the one end 13a of the third magnetic core 13 in the third pattern.

In one aspect, in the recess into which the irradiation target 51 is inserted, in addition to the magnetic flux emitted from the one end 13a of the third magnetic core 13, a strong magnetic flux may be formed by the coil 10. For that reason, the large magnetic flux density can be achieved in the hollow space, and the magnetic flux can be effectively irradiated to the irradiation target 51 inserted into the hollow space, for example, at a magnetic flux density of up to 30 mT. In one aspect, magneto-sensitive heating particles may be provided to the irradiation target 51 prior to irradiation. In this aspect, the magneto-sensitive heating particles in the irradiation target 51 may be magnetically heated by the magnetic flux, and the irradiation target 51 heated by the heat generation of the magneto-sensitive heating element when exposed to the magnetic flux.

In one aspect, according to the above-described fourth example, because the third magnetic core 13 may be inserted inside the coil 10 after the first magnetic core 11 (or the second magnetic core 12) is removed from the interior of the coil 10, it is possible to easily change the irradiation pattern of the magnetic flux from the first pattern (or second magnetic pattern) to the third pattern, depending on the relative position of the magnetic flux irradiation device 102 with respect to the irradiation target 31 or 51.

In another aspect, according to this example, when the third magnetic core 13 is positioned within the coil 10, strong magnetic flux can be formed by the coil 10 within the recess formed at a position that faces the one end 13a of the third magnetic core 13 within the coil 10. In some instances, when the third magnetic core 13 is inserted inside the coil 10 in place of the first magnetic core 11 or the second magnetic core 12, a large magnetic flux density can be achieved in the recess, and it may be possible to more effectively irradiate the magnetic flux to the irradiation target 51 that can be inserted inside the hollow space.

In addition, in this example, the columnar portion 13b of the small cross-sectional area and the columnar portion 13c of the large cross-sectional area of the third magnetic core 13 have a columnar portion shape, respectively, but are not limited thereto, and they may have a prismatic shape, respectively.

A fifth example will be described referring to FIG. 12.

FIG. 12 is a schematic side cross-sectional view illustrating a magnetic flux irradiation device according to a fifth example.

In one aspect, as illustrated in FIG. 12, a magnetic flux irradiation device 103 according to the fifth example may have the second magnetic core 12 positioned within the coil 10 in place of the first magnetic core 11 of the magnetic flux irradiation device 102 according to the fourth example. The configuration of the second magnetic core 12 is similar to the second magnetic core 12 in the third example illustrated in FIGS. 7 to 9.

Other configurations are substantially the same as those of the fourth example illustrated in FIGS. 10 and 11. In FIG. 12, the same parts as those of the fourth example illustrated in FIGS. 10 and 11 are denoted by the same reference numerals, and the detailed description thereof will not be provided.

In one aspect, according to the above-described fifth example, because the third magnetic core 13 may be inserted inside the coil 10 after the second magnetic core 12 is removed from the interior of the coil 10, it is possible to easily change the irradiation pattern of the magnetic flux from the second pattern to the third pattern, depending on the relative position of the magnetic flux irradiation device 103 with respect to the irradiation target 41 or 51.

In one aspect, according to this example, as illustrated in FIG. 11, when the third magnetic core 13 is inserted inside the coil 10, a recess may be formed at a position that faces the one end 13a of the third magnetic core 13 within the coil 10, and within the recess, in addition to the magnetic flux emitted from the one end 13a of the third magnetic core 13, strong magnetic flux can be formed by the coil 10. In some cases, when the third magnetic core 13 is inserted inside the coil 10 in place of the second magnetic core 12, large magnetic flux density can be achieved in the recess, and it may be possible to more effectively irradiate the magnetic flux to the irradiation target 51 that can be inserted inside the hollow space. In some cases, according to this example, as illustrated in FIG. 9, when the second magnetic core 12 is inserted inside the coil 10, the magnetic flux formed inside the second magnetic core 12 may be emitted in the axial direction from the one end 12a of the second magnetic core 12, after being kept in a state of being parallel to the axial direction, over a long distance by which the columnar portion 12b of the small diameter of the second magnetic core 12 protrudes with respect to the one end 10a of the coil 10. In some cases, because the second magnetic core 12 may be inserted inside the coil 10 in place of the third magnetic core 13, the diffusion start position of the magnetic flux irradiated from the one end of the magnetic core can be extended, and it may be possible to effectively irradiate the magnetic flux, even with respect to the irradiation target 41 to which the one end 13a of the third magnetic core 13 cannot be brought sufficiently closer.

Figure 13:
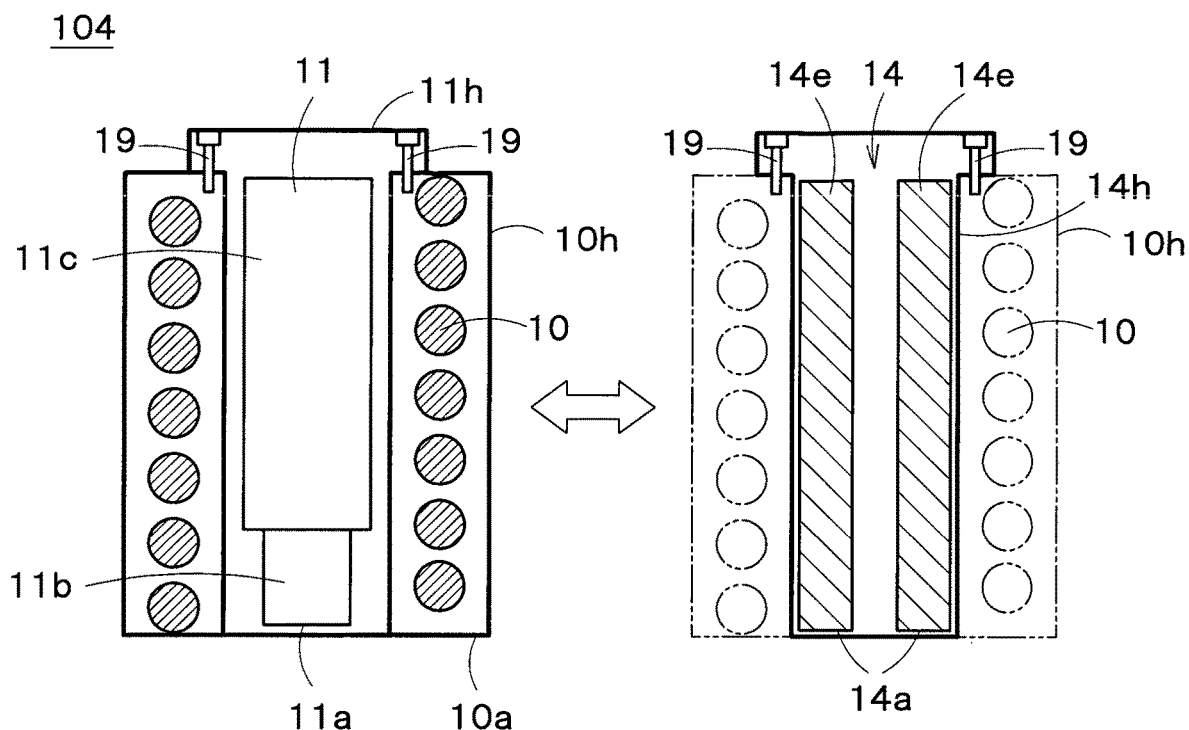
FIG. 13 is a schematic side cross-sectional view illustrating a magnetic flux irradiation device according to a sixth example.
Figure 14:
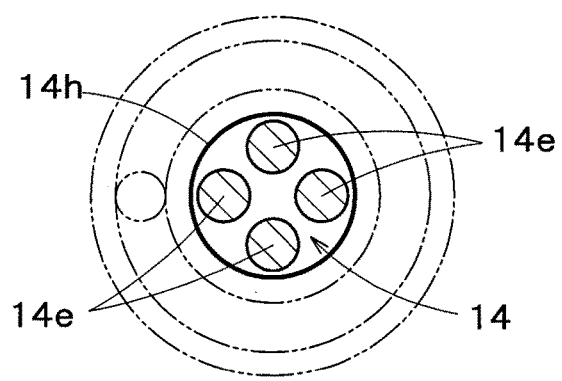
FIG. 14 is a schematic top cross-sectional view illustrating a fourth magnetic core of the magnetic flux irradiation device of FIG. 13.

A sixth example will be described referring to FIGS. 13 to 16. FIG. 13 is a schematic side cross-sectional view illustrating a magnetic flux irradiation device according to the sixth example. FIG. 14 is a schematic top cross-sectional view illustrating a fourth magnetic core of the magnetic flux irradiation device of FIG. 13. FIG. 15 is a graph illustrating the density of the magnetic flux irradiated from the first magnetic core and the fourth magnetic core in the magnetic flux irradiation device of FIG. 13. FIG. 16 is a diagram for illustrating an aspect in which magnetic flux is irradiated from the fourth magnetic core of the magnetic flux irradiation device of FIG. 13.

In one aspect, as illustrated in FIG. 13, a magnetic flux irradiation device 104 according to the sixth example may have a fourth magnetic core 14 in place of the first magnetic core 11 of the magnetic flux irradiation device 101 according to the third example above.

In one aspect, as illustrated in FIG. 14, the fourth magnetic core 14 may have four fourth columnar portion magnetic core elements 14e that can be uniformly disposed circumferentially within a central cavity defined by the coil 10. For example, each of the fourth magnetic core elements 14e may have a cylindrical shape having a diameter of 15 mm and an axial length of 120 mm. In other examples, the fourth magnetic core elements 14e may have cylindrical shape or a prismatic shape. In some examples, the fourth magnetic core elements 14e may have smaller or larger dimensions as discussed above. In some examples, the material of each of the fourth magnetic core elements 14e may be as discussed above for magnetic cores 11, 12, and 13. For example, the material of each of the fourth magnetic core elements 14e may be a Mn—Zn ferrite material. In some instances, as in the illustrated example, the fourth magnetic core elements 14e may be disposed to be spaced apart from each other, but are not limited thereto. In other instances, the fourth magnetic core elements 14e may be disposed to abut against each other. In some cases, the magnetic core cross-sectional area increases as the number of magnetic core elements increases, which may lead to distribution (decline) of the magnetic flux density.

In one aspect, as illustrated in FIG. 13, in a state in which the fourth magnetic core 14 is inserted inside the coil 10 to be parallel to the axis of the coil 10, the one end 14a of the fourth magnetic core 14 (that is, the one end of each of the fourth magnetic core elements 14e) may be adapted to be located on the same plane as the one end 10a of the coil 10.

In one aspect, where the fourth magnetic core 14 is inserted inside the coil 10, when the alternating current is supplied to the coil 10 from the power source at a predetermined frequency, alternating magnetic flux parallel to the axial direction may formed on each of the fourth magnetic core elements 14e of the fourth magnetic core 14 inserted inside the coil 10, and the alternating magnetic flux may be irradiated in the axial direction from the one end 14a of the fourth magnetic core 14 in a fourth pattern (magnetic flux density).

FIG. 15 is a graph illustrating the density of the magnetic flux irradiated from the first magnetic core 11 and the fourth magnetic core. 14 in the magnetic flux irradiation device 104 according to this example. In FIG. 15, a horizontal axis represents an axial distance starting from the one end 10a of the coil 10, L1 represents a density of the magnetic flux irradiated from the one end 11a of the first magnetic core 11, and L4 represents a density of the magnetic flux irradiated from the one end 14a of the fourth magnetic core 14.

In one aspect, as illustrated in FIG. 15, the density of the magnetic flux irradiated from the one end 14a of the fourth magnetic core 14 is less likely to be attenuated (magnetic flux is less likely to be diffused), as compared to the density of the magnetic flux irradiated from the one end 11a of the first magnetic core 11. In some cases, where the fourth magnetic core 14 is inserted inside the coil 10 in place of the first magnetic core 11, the diffusion of the magnetic flux irradiated from the one end of the magnetic core can be suppressed.

In one aspect, as discussed above with respect to magnetic cores 11, 12, and 13, magnetic core 14 may be detachably connected to the coil 10. For example, the fourth magnetic core 14 may be adapted to be fixed to the coil 10 using the screw 19 or some other mechanism as discussed above.

For example, as illustrated in FIG. 13, the fourth magnetic core 14 may be coaxially housed within the fourth magnetic core housing 14h that can be inserted inside the cavity of the coil housing 10h. In some cases, a flange extending radially outward from the cavity of the coil housing 10h may be provided at the other end of the fourth magnetic core housing 14h, and when the flange is in close contact with the other end of the coil housing 10h, the screw 19 passing through the flange may be fitted into the screw hole provided in the coil housing 10h. In some instances, where the fourth magnetic core 14 is inserted inside the coil 10, the relative position of the fourth magnetic core 14 with respect to the coil 10 is kept at a predetermined position (fixed).

Other configurations are substantially the same as those of the third example illustrated in FIGS. 7 to 10. In FIGS. 13 and 14, the same parts as those of the third example illustrated in FIGS. 7 to 10 are denoted by the same reference numerals, and the detailed description thereof will not be provided.

Next, the operation of the above-described example will be described.

In one aspect, as illustrated in FIG. 8(*a*), the irradiation target 31 may be located inside the irradiation object 30 having a convex shape. In some instances, as illustrated in FIG. 16, the irradiation target 61 may be located at the bottom of an irradiation object 60 having a concave shape (in particular, the irradiation target 61, the surrounding structure of which projects to block the upper part).

For example, in some instances, the first magnetic core 11 (or magnetic cores 12 or 13) may be removed from the interior of the coil 10, and the fourth magnetic core 14 may be inserted inside the coil 10 to be parallel to the axis of the coil 10. The fourth magnetic core may be detachably connected to the coil 10 via the mechanisms described above (such as by the screw 19 or another mechanism).

In one aspect, the one end 14a of the fourth magnetic core 14 inserted inside the coil 10 may be disposed to face the irradiation target 61. In some cases, because the coil 10 physically interferes with the structure around the irradiation target 61, it is not possible to bring the one end 14a of the fourth magnetic core 14 as close to the irradiation target 61 (for example, up to the position of 5 mm from the irradiation target 61). In one aspect, the one end 14a may be positioned to be spaced from the irradiation target 61, for example, by up to 15 cm, depending on the size of the coil 10 and the magnetic core 14. In one example, the one end 14a may be positioned to be spaced from the irradiation target 61 by up to 30 mm.

In one aspect, the alternating current may be supplied to the coil 10 from a power source (not illustrated) at a predetermined frequency (for example, 50 kHz to 40 kHz, such as 100 kHz). Alternating magnetic flux parallel to the axial direction may be formed on each of the fourth magnetic core elements 14e of the fourth magnetic core 14 inserted inside the coil 10, and the alternating magnetic flux may be irradiated to the irradiation target 61 from the one end 14a of the fourth magnetic core 14 in the fourth pattern.

In some instances, as illustrated in FIG. 15, the magnetic flux irradiated from the one end 14a of the fourth magnetic core 14 may be less likely to be diffused (magnetic flux density is less likely to be attenuated). For that reason, even if the one end 14a of the fourth magnetic core 14 is positioned at a position spaced from the irradiation target 61 by 30 mm, the irradiation target 61 can be effectively irradiated with the magnetic flux, for example, at a magnetic flux density of 10 mT. In one aspect, magneto-sensitive heating particles may be provided to the irradiation target 61 prior to irradiation. In this aspect, the magneto-sensitive heating particles in the irradiation target 61 may be magnetically heated by the magnetic flux, and the irradiation target 61 heated by the heat generation of the magneto-sensitive heating element when exposed to the magnetic flux.

In one aspect, according to the above-described sixth example, because the fourth magnetic core 14 may be inserted inside the coil 10 after the first magnetic core 11 is removed from the interior of the coil 10, it is possible to easily change the irradiation pattern of the magnetic flux from the first pattern to the fourth pattern, depending on the relative position of the magnetic flux irradiation device 104 with respect to the irradiation target 31 or 61.

In one aspect, according to this example, when the fourth magnetic core 14 is inserted inside the coil 10, the magnetic flux emitted from the one end 14*a* of the fourth magnetic core 14 may be less likely to be diffused (the magnetic flux density is less likely to be attenuated). For that reason, because the fourth magnetic core 14 may be inserted inside the coil 10 in place of the first magnetic core 11, the diffusion of the magnetic flux irradiated from the one end of the magnetic core can be suppressed, and it may be possible to effectively irradiate the magnetic flux, even with respect to the irradiation target 61 to which the one end 11*a* of the first magnetic core 11 cannot be brought sufficiently closer.

In one aspect, where the structure around the irradiation target 61 protrudes to block the upper of the irradiation target 61 as illustrated in FIG. 16, because it is not possible to bring the one end 12*a* of the second magnetic core 12 close to the irradiation target 61, the second magnetic core 12 of the third example and the fifth example described above may not effectively irradiate the target 61. However, by inserting the fourth magnetic core 14 into the device 104, even if it is not possible to bring the one end 14*a* of the fourth magnetic core 14 close to the irradiation target 61, the fourth magnetic core 14 according to the sixth example may effectively irradiate the target 61.

For example, when the irradiation target is spaced from the one end 10*a* of the coil 10 by 20 mm or more, because it is difficult to keep the diffusion suppression effect of the magnetic flux by 20 mm or more, the second magnetic core 12 in the third example and the fifth example described above may not effectively irradiate the target 61. In another example, because it is possible to keep the diffusion suppression effect of the magnetic flux up to a distance of 20 mm or more from the first end 14*a* of the fourth magnetic core 14, the fourth magnetic core 14 of the sixth example may effectively irradiate the target 61.

In one aspect, as shown in this example, the number of the fourth magnetic core elements 14*e* may be four, but is not limited thereto. In other examples, the number of the fourth magnetic core elements 14*e* may be two or three or five or more.

Furthermore, in this example, each of the fourth auxiliary magnetic core elements 14*e* has a cylindrical shape, but is not limited thereto, and they may have a prismatic shape.

This example was described with respect to the first magnetic core 11 having the columnar portion of the small cross-sectional area that defines the one end, and the columnar portion of the large cross-sectional area adjacent to the columnar portion of the small cross-sectional area. In other examples, the second magnetic core 12 or the third magnetic core 13 described above may also be employed in place of the first magnetic core 11.

Figure 17:
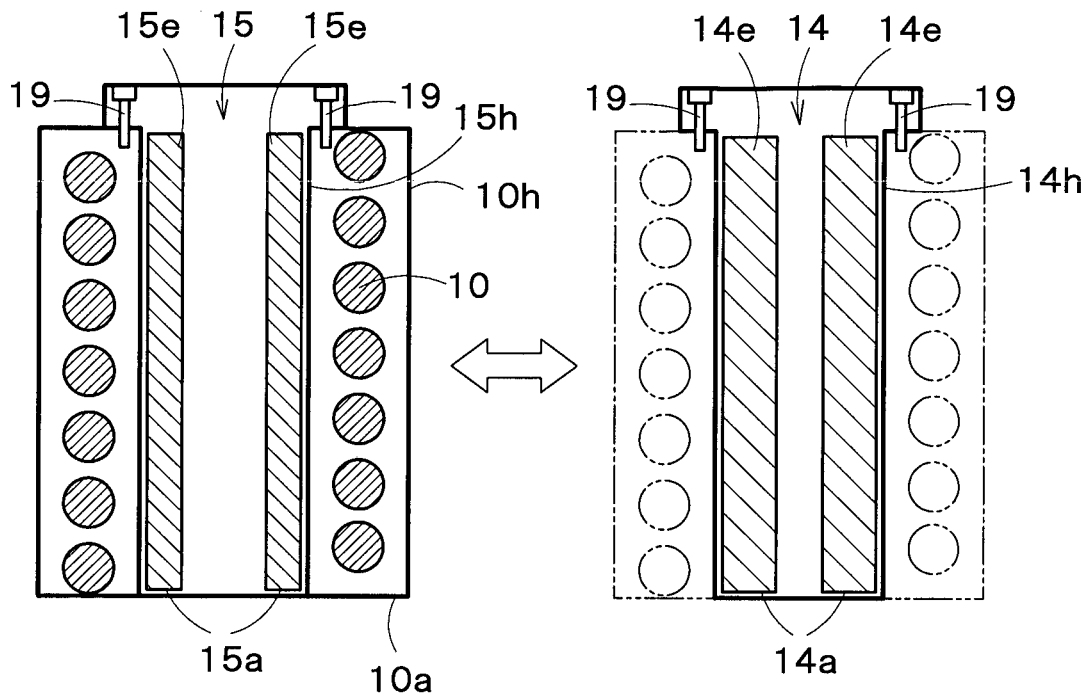
FIG. 17 is a schematic side cross-sectional view illustrating a magnetic flux irradiation device according to a seventh example.
Figure 18:
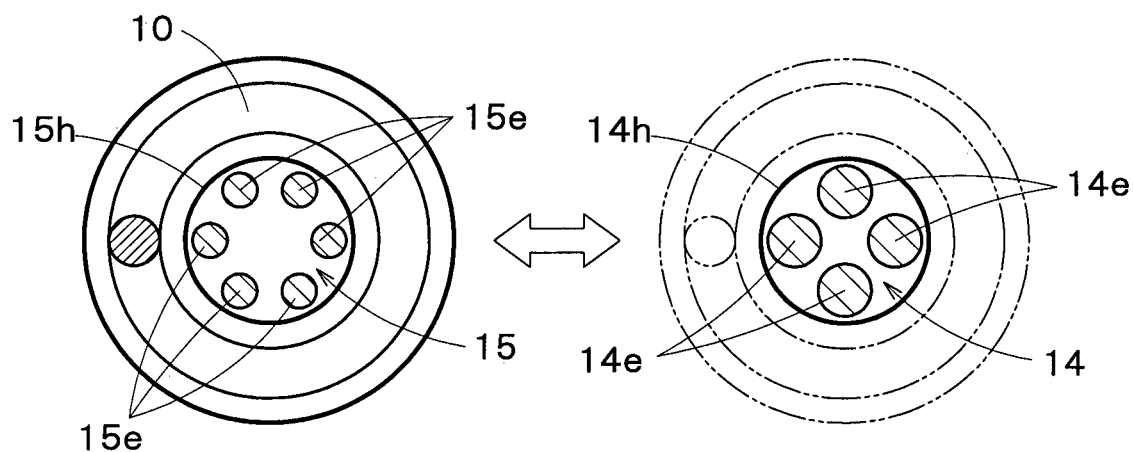
FIG. 18 is a top cross-sectional view illustrating the magnetic flux irradiation device of FIG. 17.

A seventh example will be described referring to FIGS. 17 and 18. FIG. 17 is a schematic side cross-sectional view illustrating a magnetic flux irradiation device according to the seventh example. FIG. 18 is a schematic top cross-sectional view illustrating the magnetic flux irradiation device of FIG. 17.

In one aspect, as illustrated in FIGS. 17 and 18, a magnetic flux irradiation device 105 according to the seventh example may have a fifth magnetic core 15 in place of the fourth magnetic core 14 of the magnetic flux irradiation device 104 according to the sixth example.

In one aspect, as illustrated in FIG. 18, the fifth magnetic core 15 may have six fifth cylindrical core elements 15*e* that can be uniformly disposed circumferentially within a cavity defined by the coil 10. In various examples, the shape and material of the fifth cylindrical core elements 15*e* may be as described above in the sixth example for the fourth cylindrical core elements 14*e*. In one example, each of the fifth magnetic core elements 15*e* may have a cylindrical shape having a diameter of 10 mm and an axial length of 120 mm. The material of each of the fifth magnetic core elements 15*e* may be, for example, a Mn—Zn ferrite material. In some instances, as illustrated in the example, the fifth magnetic core elements 15*e* may be disposed to be spaced apart from each other, but are not limited thereto. In some instances, the fifth magnetic core elements 15*e* may be disposed to abut against each other. In one aspect, the magnetic core cross-sectional area increases as the number of magnetic core elements increases, which may lead to distribution (decline) of the magnetic flux density.

In one aspect, as illustrated in FIG. 17, the one end 15*a* of the fifth magnetic core 15 may be located on the same plane as the one end 10*a* of the coil 10.

In one example, where the fifth magnetic core 15 is inserted inside the coil 10, when the alternating current is supplied to the coil 10 from the power source at a predetermined frequency, the alternating magnetic flux parallel to the axial direction may be formed on each of the magnetic core elements 15*e* of the fifth magnetic core 15 inserted inside the coil 10, and the alternating magnetic flux may be irradiated in the axial direction from the one end 15*a* of the fifth magnetic core 15 in the fifth pattern (magnetic flux density).

The fifth magnetic core 15 may be inserted inside the coil 10 and may be detachably connected to the coil 10 as described above for magnetic cores 11 to 14. For example, the fifth magnetic core 15 may be adapted to be fixed to the coil 10 using the screw 19.

For example, as illustrated in FIG. 17, the fifth magnetic core 15 may be coaxially housed within the fifth magnetic core housing 15*h* that can be inserted into the cavity of the coil housing 10*h*. At the other end of the fifth magnetic core housing 15*h*, a flange extending radially outward from the cavity of the coil housing 10*h* may provided. When the flange is in close contact with the other end of the coil housing 10*h*, the screw 19 passing through the flange may be fitted into the screw hole provided in the coil housing 10*h*. Thus, where the fifth magnetic core 15 is inserted inside the coil 10, the relative position of the fifth magnetic core 15 with respect to the coil 10 is kept at a predetermined position (fixed).

Other configurations are substantially the same as those of the sixth example illustrated in FIGS. 13 to 16. In FIGS. 17 and 18, the same parts as those of the sixth example illustrated in FIGS. 13 to 16 are denoted by the same reference numerals, and the detailed description thereof will not be provided.

In one aspect, according to the above-described seventh example, when the fourth magnetic core 14 is inserted inside the coil 10 after the fifth magnetic core 15 has been removed from the interior of the coil 10, it is possible to easily change the irradiation pattern of the magnetic flux from the fifth pattern to the fourth pattern, depending on the relative position of the magnetic flux irradiation device 105 with respect to the irradiation target.

In another aspect, according to this example, because the number of the fourth magnetic core elements 14e is different from the number of the fifth magnetic core elements 15e, the irradiation distance of the magnetic flux irradiated from the one end of the magnetic core is different and can be easily changed by inserting the fifth magnetic core 15 in place of the fourth magnetic core 14 (or magnetic cores 11 to 13).

In one example, the number of the fourth magnetic core elements 14e may be four. In another example, the number of fifth magnetic core elements 15e may be six. However, the number of magnetic core elements in either may be some other number. For example, as long as the number of the fourth magnetic core elements 14e and the number of the fifth magnetic core elements 15e are different from each other, the number is not limited to the combination of these numbers. In one aspect, if the number of magnetic core elements is different from one magnetic core to another, the magnetic cores will have different magnetic flux irradiation patterns.

In one aspect, as in this example, each of the fifth auxiliary magnetic core elements 15e may have a cylindrical shape. In other examples, the fifth auxiliary magnetic core elements 15e may have a prismatic shape.

Figure 21:
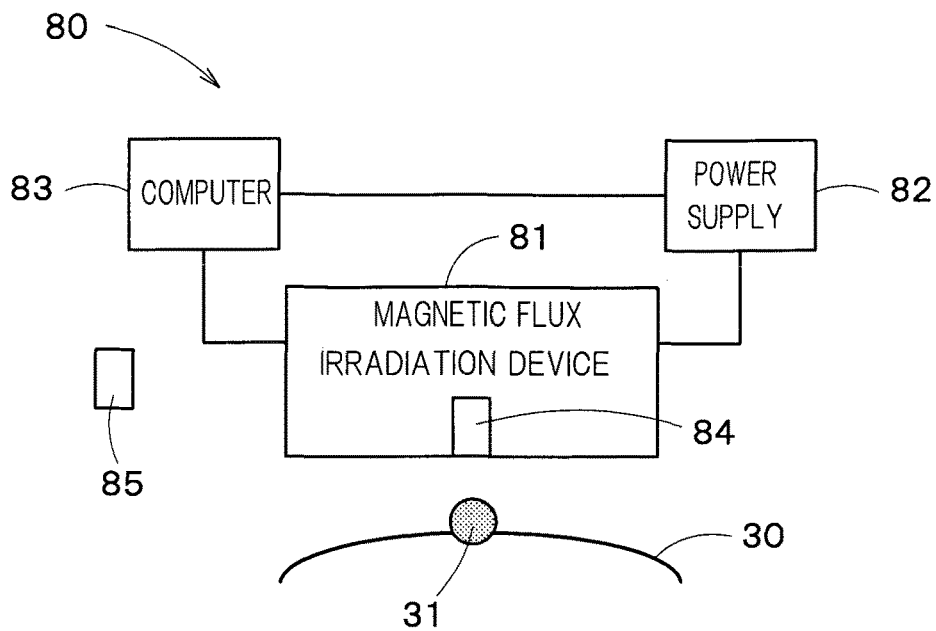
FIG. 21 is a schematic of a system including a magnetic flux irradiation device according to various examples.

FIG. 21 is a block diagram illustrating systems for using the magnetic flux irradiation devices described in detail in Section II. For example, the system 80 includes a magnetic flux irradiation device 81 having a coil 10 and a first magnetic core 84 disposed within a central cavity of the coil 10. The first magnetic core is detachably connected to the device 81. The device 81 can be any of the example devices described previously in Section II and any variations thereof as within the scope of this disclosure. The system 80 also includes a power supply 62 configured to supply electrical current to the coil 10 of the magnetic flux irradiation device 81. In some instances, the power supply 82 is configured to supply alternating current to the coil 10. The system 80 also includes a computer 83 configured to perform at least one of control operation of the magnetic flux irradiation device 81 or process data obtained from monitoring an irradiation target 31 upon which the magnetic flux irradiation device 81 is used. While irradiation target 31 is used for illustrative purposes in FIG. 19, alternatively, irradiation targets 41, 51, or 61 may also be irradiated using system 60. In another aspect, the system 80 may include a second magnetic core 85. The first magnetic core 84 may be replaced by a second magnetic core 85 in the magnetic flux irradiation device 81. The first magnetic core 84 and the second magnetic core 85 can be any of the example magnetic cores described previously in Section II and any variations thereof as within the scope of this disclosure.

In one aspect, the magnetic flux irradiation device 81 contains a magnetic core 84 or 85 selected based on, for example, characteristics of the irradiation target 31 or the desired magnetic flux density. As discussed above, different magnetic core configurations may provide different irradiation patterns. For example, different magnetic core configurations may be configured to emit magnetic flux at different magnetic flux densities. In some examples, different magnetic core configurations may be configured to emit magnetic flux that has different extents of diffusion (attenuation). Based on the irradiation pattern desired to irradiate the irradiation target 31, the magnetic flux irradiation device 81 may contain the first magnetic core 84 or second magnetic core 85.

In one aspect, when the power supply 82 is activated and supplies alternating current to the coil 10, alternating magnetic flux is generated on the magnetic core. In one aspect, the alternating magnetic flux is emitted from the first end of the magnetic core and can irradiate an irradiation target 31 (such as a tumor) of an irradiation object 30 (such a subject with a tumor) that is positioned to face the first end of the magnetic core.

In some instances, the computer 83 may be configured to control the power supply 82. In other instances, the computer 83 may be configured to monitor the alternating current supplied to the coil 10 by the power supply 82. In some cases, the computer 83 may be configured to receive data about the irradiation object 30 or the irradiation target 31. For example, the computer 83 may be configured to process visual or temperature data obtained from monitoring the irradiation target 31. In other instances, the computer 83 may be configured to receive data such as the type of magnetic core positioned within the magnetic core of the magnetic flux irradiation device 81 or characteristics about the irradiation target 31 or irradiation object 30. In other instances, the computer 83 may be configured to contain information about the types of magnetic cores that may be inserted into the magnetic flux irradiation device 81. In some instances, the computer 83 is configured to perform more than one of the functions described in this paragraph or one of the described functions and some other function relating to use of the device 81.

The computer 83 may be a variety of different computing devices for storing and processing data. The computer 83 may comprise, for example, a smartphone, tablet, e-reader, laptop computer, desktop computer, or a gaming device. In some embodiments, the computing device may comprise a processor interfaced with other hardware via a bus. A memory, which can include any suitable tangible (and non-transitory) computer-readable medium such as RAM, ROM, EEPROM, or the like, can embody program components that configure operation of the computer 83. The computing device may also comprise input/output interface components (for example, a display, keyboard, touch-sensitive surface, and mouse) and additional storage.

In some instances, the computer 83 may comprise a communication device. The communication device may comprise one or more of any components that facilitate a network connection. For example, the communication device may be wireless and may comprise wireless interfaces such as IEEE 802.11, Bluetooth, or radio interfaces for accessing cellular telephone networks (for example, transceiver/antenna for accessing a CDMA, GSM, UMTS, or other mobile communications network). In some cases, the communication device may be wired and may comprise interfaces such as Ethernet, USB, or IEEE 1394.

The system 80 may include additional computers each of which perform distinct functions such as those described above or other functions useful to the use of the system 80 to irradiate an irradiation target 31.

Figure 22:
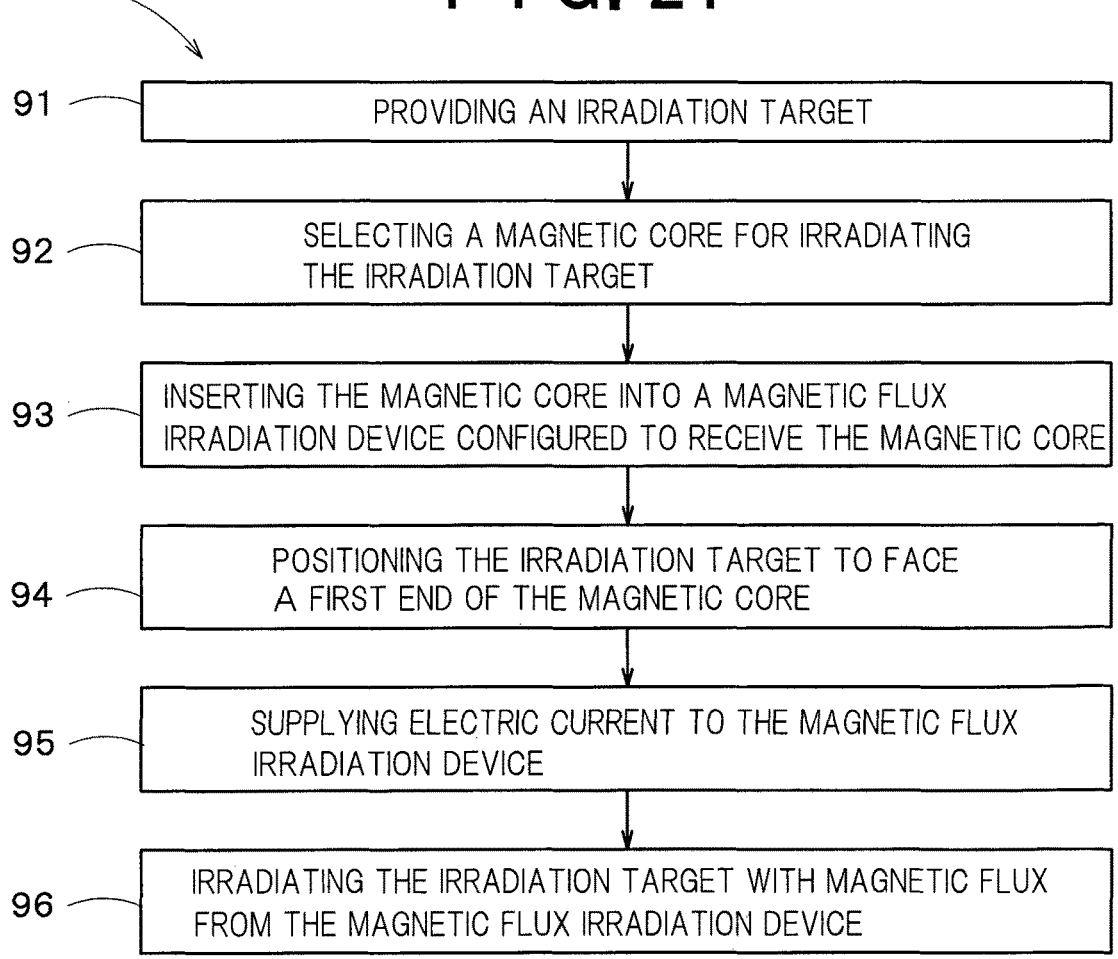
FIG. 22 is a block diagram of a method of irradiating an irradiation target of an irradiation object using a magnetic flux irradiation device according to various examples.

FIG. 22 is a block diagram illustrating methods for using the magnetic flux irradiation devices described in detail in Section II. In one aspect, the method 90 is a method of irradiating an irradiation target with magnetic flux. Methods of irradiating an irradiation target with magnetic flux as described herein may be useful for treating a subject with a tumor.

In block 91, an irradiation target is provided. In one aspect, the irradiation target is on the surface of or within an irradiation object. For example, the irradiation target may be a tumor of an irradiation subject.

In block 92, a magnetic core for irradiating the irradiation target is selected. In one aspect, the magnetic core selected for use in the method 90 based on the nature of the irradiation target to be irradiated. For example, the irradiation target may be on the surface of the irradiation object or just below the surface of the irradiation object, and the surface of the irradiation object may be relatively flat or may be convex. In this instance, a magnetic flux irradiation device in which the first end of the magnetic core is on the same plane as the first end of the coil may be provided (for example, as shown in FIG. 7). Alternatively, a magnetic flux irradiation device in which the first end of the magnetic core is recessed axially with respect to the first end of the coil may be provided (for example, as shown in FIG. 11).

In another example, the irradiation target may be on the surface of the irradiation object or just below the surface of the irradiation object but the structure of the irradiation object may obstruct access to the irradiation target. In this instance, a magnetic flux irradiation device in which the first end of the magnetic core is protruded axially with respect to the first end of the coil may be provided (for example, as shown in FIG. 9). In this instance, the smaller cross-section of the magnetic core as compared to the diameter of the coil permits the magnetic core to be brought within sufficient proximity to the irradiation target to be irradiated with a desired magnetic flux density. Alternatively, a magnetic flux irradiation device that includes a distributed magnetic core may be provided (for example, as shown in FIGS. 13 to 18) and positioned at a further distance from the irradiation target. In this instance, the magnetic flux density may have reduced attenuation (dissipation) as it is emitted from the first end of the magnetic core such the irradiation target may still be irradiated with the desired magnetic flux density even though there is a greater distance between the first end of the magnetic core and the irradiation target.

In block 93, the selected magnetic core is inserted into a magnetic flux irradiation device configured to receive the magnetic core. The magnetic flux irradiation device may be one of the devices specifically described in the examples provided in Section II of this disclosure or may be variations thereof as within the scope of this disclosure.

In block 94, the irradiation target is positioned to face a first end of the magnetic core. In another aspect, the irradiation target may be positioned within a certain proximity of the first end of the magnetic core. For example, the irradiation target may be positioned at a distance of about 5 mm, 10 mm, 20 mm, 30 mm, 50 mm, 100 mm, or some other distance up to about 15 cm from the first end of the magnetic core. Where the irradiation target is inserted within the magnetic core, it may be positioned to not be in contact with the magnetic core or any other part of the device.

In block 95, electric current is supplied to magnetic flux irradiation device. In block 96, the irradiation target is irradiated with magnetic flux. In one aspect, the irradiation target can be irradiated with magnetic flux when electrical current is supplied to the coil (such as from a power supply) to generate magnetic flux on the magnetic core that is emitted from the first end of the magnetic core and irradiated to the irradiation target. In another aspect, the irradiation target may be positioned in sufficient proximity to the first end of the magnetic core so as to receive a desired magnetic flux density. In one aspect, the irradiation target is irradiated with a magnetic flux density of about 0.5 mT to about 30 mT. For instance, the magnetic flux density can be about 5 mT, about 10 mT, about 15 mT, about 20 mT, about 25 mT, or about 30 mT, or other densities within this range.

In some instances, magneto-sensitive heating particles may be provided to the irradiation target prior to irradiation. In some instances, the irradiation target may contain a magneto-sensitive heating particles that heat when exposed to magnetic flux. In one aspect, the magneto-sensitive heating particles may be injected into the irradiation target. For example, the magneto-sensitive heating particles in the irradiation target may be magnetically heated by the magnetic flux, and the irradiation target heated by the heat generation of the magneto-sensitive heating element when exposed to the magnetic flux. In one example, magneto-sensitive heating particles can include magnetite particles. In another example, the magneto-sensitive heating particles may be magnetic cationic liposomes. However, a range of materials can be used to prepare magneto-sensitive heating particles and this disclosure is not limited to those described.

The foregoing description of certain embodiments, including illustrated embodiments, has been presented only for the purpose of illustration and description and is not intended to be exhaustive or to limit the disclosure to the precise forms disclosed. Numerous modifications, adaptations, and uses thereof will be apparent to those skilled in the art without departing from the scope of the disclosure. Certain features that are described in this disclosure in the context of separate embodiments can also be implemented in combination in a single implementation. Conversely, various features that are described in the context of a single implementation can also be implemented in multiple ways separately or in any suitable subcombination. Moreover, although features may be described above as acting in certain combinations, one or more features from a combination can in some cases be excised from the combination, and the combination may be directed to a subcombination or variation of a subcombination. Thus, particular embodiments have been described. Other embodiments are within the scope of the disclosure.

All printed patents and publications referred to in this application are hereby incorporated herein in their entirety by this reference.

REFERENCE SIGNS LIST

101 magnetic flux irradiation device
102 magnetic flux irradiation device
103 magnetic flux irradiation device
104 magnetic flux irradiation device
105 magnetic flux irradiation device
10 coil
10*a* one end of the coil
10*h* coil housing
11 first magnetic core
11*a* one end of the first magnetic core
11*b* columnar portion of small cross-sectional area
11*c* columnar portion of large cross-sectional area
11*h* first magnetic core housing
12 second magnetic core
12*a* one end of the second magnetic core
12*b* columnar portion of small cross-sectional area
12*c* columnar portion of large cross-sectional area
12*h* second magnetic core housing 13 third magnetic core
13a one end of the third magnetic core
13b columnar portion of small cross-sectional area
13c columnar portion of large cross-sectional area
13h third magnetic core housing
14 fourth magnetic core
14a one end of the fourth magnetic core
14e fourth magnetic core element
14h fourth magnetic core housing
15 fifth magnetic core
15a one end of the fifth magnetic core
15e fifth magnetic core element
15h fifth magnetic core housing
19 screw made of resin
201 magnetic flux irradiation device
202 magnetic flux irradiation device
20 coil
20a one end of the coil
20h coil housing
20s coil side screw
21 magnetic core
21a one end of the magnetic core
21h magnetic core housing
21s magnetic core side screw
21s' magnetic core side screw
22 auxiliary magnetic core
22a one end of the auxiliary magnetic core
22h auxiliary magnetic core housing
22s auxiliary magnetic core side screw
30, 40, 50, 60 irradiation object
31, 41, 51, 61 irradiation target

What is claimed is:

1. A device comprising:
a magnetic flux irradiation device comprising:
    a cylindrical coil, the cylindrical coil configured to receive a plurality of different magnetic cores; and
    a first magnetic core disposed within the cylindrical coil and parallel to an axis of the cylindrical coil, wherein the first magnetic core is configured to be detachably connected to the cylindrical coil,
wherein the magnetic flux irradiation device is configured to irradiate magnetic flux with a first irradiation pattern from a first end of the magnetic flux irradiation device when electric current is supplied to the cylindrical coil, the first irradiation pattern generated based on a configuration of the first magnetic core; and
wherein the magnetic flux irradiation device is configured to be positioned adjacent to and oriented with the first end towards an irradiation target external to the magnetic flux irradiation device, and to apply the first irradiation pattern to the irradiation target.

2. The device of claim 1, wherein the magnetic flux irradiation device comprises a second magnetic core, and wherein the first magnetic core may be replaced by the second magnetic core, wherein the magnetic flux irradiation device is configured to irradiate magnetic flux with a second irradiation pattern from a first end of the second magnetic core when electric current is supplied to the cylindrical coil when the second magnetic core is installed, the second irradiation pattern generated based on a configuration of the second magnetic core.

3. The device according to claim 2, wherein the first magnetic core and the second magnetic core are detachably connectable to the cylindrical coil by:
    a screw made of nonconductive material;
    a screw system comprising a first screw threaded part attached to the first magnetic core, a second screw threaded part attached to the second magnetic core, and a third screw threaded part attached to the cylindrical coil, wherein the first screw threaded part and the second screw threaded part are matched to the third screw threaded part, and wherein each of the first, second, and third threaded parts are made of nonconductive material;
    a clip system;
    a molded retention finger system;
    a wedge system; or
    a layer of adhesive or sealant.

4. The device according to claim 2, wherein the first magnetic core or the second magnetic core has a columnar portion of a first cross-sectional area that defines the first end of the first magnetic core or the first end of the second magnetic core, and a columnar portion of a second cross-sectional area adjacent to the columnar portion of the first cross-sectional area, the first cross-sectional area smaller than the second cross-sectional area.

5. The device according to claim 2, wherein the first end of the first magnetic core:
    is positioned on a same plane as a first end of the cylindrical coil;
    protrudes axially outward from a first end of the cylindrical coil; or
    is receded axially from a first end of the cylindrical coil.

6. The device according to claim 2, wherein the coil defines a central cavity, wherein the first magnetic core comprises a plurality of magnetic core elements uniformly disposed circumferentially within the central cavity of the cylindrical coil.

7. The device according to claim 6, wherein the first magnetic core comprises 2 to 10 magnetic core elements.

8. The device according to claim 2, wherein the configuration of the first magnetic core is different that the configuration of the second magnetic core.

9. A system comprising:
    the device according to claim 1;
    a power supply configured to supply electrical current to the cylindrical coil of the magnetic flux irradiation device; and
    a computer configured to control operation of the magnetic flux irradiation device or process data obtained from monitoring an irradiation target upon which the magnetic flux irradiation device is used.

10. The system of claim 9, further comprising a second magnetic core configured to be disposed within the cylindrical coil and parallel to the axis of the cylindrical coil in place of the first magnetic core.

11. A method of irradiating an irradiation target with magnetic flux, the method comprising:
    (a) providing an irradiation target;
    (b) selecting a magnetic core to irradiate the irradiation target;
    (c) inserting the selected magnetic core into a magnetic flux irradiation device, thereby providing the device according to claim 1;
    (d) positioning the irradiation target to face the first end of the magnetic core; and
    (e) irradiating the irradiation target with magnetic flux by supplying electrical current to the cylindrical coil to generate magnetic flux on the magnetic core that is emitted from the first end of the magnetic core to the irradiation target, wherein the magnetic flux irradiation pattern of the magnetic core is generated based on the configuration of the magnetic core.

12. The method according to claim 11, wherein the irradiation target is positioned on the axis of the cylindrical coil.

13. The method according to claim 11, wherein the irradiation target contains magneto-sensitive heating particles that heat when exposed to magnetic flux.

* * * * *